United States Patent
Kim et al.

(10) Patent No.: US 10,981,111 B2
(45) Date of Patent: Apr. 20, 2021

(54) CARBON DIOXIDE CONVERSION REACTOR, SERIES REACTOR FOR CONVERTING AND CAPTURING CARBON DIOXIDE INCLUDING THE SAME, AND PROCESS OF CONVERTING AND CAPTURING CARBON DIOXIDE USING THE SAME

(71) Applicant: KOREA UNIVERSITY RESEARCH AND BUSINESS FOUNDATION, Seoul (KR)

(72) Inventors: Jungbae Kim, Seoul (KR); Han Sol Kim, Gyeonggi-do (KR); Sung Gil Hong, Seoul (KR)

(73) Assignee: KOREA UNIVERSITY RESEARCH AND BUSINESS FOUNDATION, Seoul (KR)

( * ) Notice: Subject to any disclaimer, the term of this patent is extended or adjusted under 35 U.S.C. 154(b) by 192 days.

(21) Appl. No.: 15/738,620

(22) PCT Filed: Jun. 24, 2016

(86) PCT No.: PCT/KR2016/006808
§ 371 (c)(1),
(2) Date: Dec. 21, 2017

(87) PCT Pub. No.: WO2016/209049
PCT Pub. Date: Dec. 29, 2016

(65) Prior Publication Data
US 2018/0185786 A1    Jul. 5, 2018

(30) Foreign Application Priority Data

Jun. 24, 2015   (KR) .......... 10-2015-0089971
Jun. 24, 2016   (KR) .......... 10-2016-0079587

(51) Int. Cl.
*C12M 3/00*     (2006.01)
*B01L 3/00*     (2006.01)
(Continued)

(52) U.S. Cl.
CPC ............. *B01D 53/84* (2013.01); *B01D 53/62* (2013.01); *B01D 53/96* (2013.01); *C12P 3/00* (2013.01);
(Continued)

(58) Field of Classification Search
CPC .................... B01D 53/84; B01D 2255/804
See application file for complete search history.

(56) References Cited

U.S. PATENT DOCUMENTS 6,143,556 A * 11/2000 Trachtenberg ......... B01D 53/62
                                                 435/289.1
7,998,714 B2 * 8/2011 Gellett ............... B01D 53/1475
                                                   435/168
(Continued)

FOREIGN PATENT DOCUMENTS

JP       2014-213275 A    11/2014
KR    10-2011-0087273 A    8/2011
(Continued)

OTHER PUBLICATIONS

Bhattacharya, S., et al., "Solubilization and Concentration of Carbon Dioxide: Novel Spray Reactors With Immobilized Carbonic Anhydrase", "Biotechnology and Bioengineering", Apr. 5, 2004, pp. 37-46, vol. 86, No. 1.
(Continued)

*Primary Examiner* — Nathan A Bowers
(74) *Attorney, Agent, or Firm* — Hultquist, PLLC; Steven J. Hultquist

(57) ABSTRACT

The present invention relates to a carbon dioxide conversion reactor and more particularly, to a carbon dioxide conversion
(Continued)

reactor capable of converting carbon dioxide contained in flue gas into an aqueous bicarbonate solution that may be used in many applications; and at the same time, preventing back pressure from increasing due to supplied flue gas by allowing a conversion process to rapidly proceed, thereby significantly reducing the level of carbon dioxide contained in flue gas with high efficiency and high conversion speed, a series reactor for converting and capturing carbon dioxide including the carbon dioxide conversion reactor, and a process of converting and capturing carbon dioxide using the carbon dioxide conversion reactor.

14 Claims, 7 Drawing Sheets

(51) Int. Cl.
  *B01D 53/00* (2006.01)
  *B01D 53/84* (2006.01)
  *B01D 53/62* (2006.01)
  *B01D 53/96* (2006.01)
  *C12P 3/00* (2006.01)

(52) U.S. Cl.
  CPC ............... *C12Y 402/01001* (2013.01); *B01D 2251/606* (2013.01); *B01D 2252/103* (2013.01); *B01D 2255/804* (2013.01); *B01D 2257/504* (2013.01); *B01D 2258/0283* (2013.01); *Y02C 20/40* (2020.08)

(56) References Cited

U.S. PATENT DOCUMENTS

| | | | | |
|---|---|---|---|---|
| 2004/0219090 | A1* | 11/2004 | Dziedzic | B01D 53/229 423/437.1 |
| 2010/0086983 | A1* | 4/2010 | Gellett | B01D 53/1475 435/168 |
| 2013/0045514 | A1* | 2/2013 | Barbero | B01D 53/62 435/131 |
| 2013/0171720 | A1 | 7/2013 | McKenna et al. | |
| 2013/0203155 | A1 | 8/2013 | Penders et al. | |
| 2014/0322803 | A1* | 10/2014 | Constantz | C01B 32/60 435/289.1 |
| 2015/0024453 | A1 | 1/2015 | Fradette et al. | |

FOREIGN PATENT DOCUMENTS

| | | |
|---|---|---|
| KR | 10-2011-0117350 A | 10/2011 |
| KR | 10-2015-0006253 A | 1/2015 |
| WO | 9855210 A1 | 12/1998 |

OTHER PUBLICATIONS

Park, J.-M., et al., "Enhancing the Production of Rhodobacter sphaeroides-Derived Physiologically Active Substances Using Carbonic Anhydrase-Immobilized Electrospun Nanofibers", "Biomacromolecules", Sep. 18, 2012, pp. 3780-3786, vol. 12.

* cited by examiner

CARBON DIOXIDE CONVERSION REACTOR, SERIES REACTOR FOR CONVERTING AND CAPTURING CARBON DIOXIDE INCLUDING THE SAME, AND PROCESS OF CONVERTING AND CAPTURING CARBON DIOXIDE USING THE SAME

CROSS-REFERENCE TO RELATED APPLICATIONS

This application is a U.S. national phase under the provisions of 35 U.S.C. § 371 of International Patent Application No. PCT/KR2016/006808 filed Jun. 24, 2016, which in turn claims priority of Korean Patent Application No. 10-2015-0089971 filed Jun. 24, 2015 and Korean Patent Application No. 10-2016-0079587 filed Jun. 24, 2016. The disclosures of such international patent application and Korean priority patent applications are hereby incorporated herein by reference in their respective entireties, for all purposes.

TECHNICAL FIELD

The present invention relates to a carbon dioxide conversion reactor, and more particularly, to a carbon dioxide conversion reactor capable of converting carbon dioxide contained in flue gas into an aqueous bicarbonate solution that may be used in many applications; and at the same time, preventing back pressure from increasing due to supplied flue gas by allowing a conversion process to proceed rapidly, thereby significantly reducing the level of carbon dioxide contained in flue gas with high efficiency and high conversion speed, a series reactor for converting and capturing carbon dioxide including the carbon dioxide conversion reactor, and a process of converting carbon dioxide using the carbon dioxide conversion reactor.

BACKGROUND ART

Traditionally, technology for capturing and storing carbon dioxide has been proposed as a method of reducing carbon dioxide. The technology for capturing and storing carbon dioxide refers to technology that captures carbon dioxide generated from emission sources such as a power plant before carbon dioxide is discharged into the atmosphere, and then transports and stores the carbon dioxide in a stable form. A step of capturing carbon dioxide consists of adsorption and desorption processes. First, in the adsorption process, carbon dioxide is captured from flue gas using an absorbent capable of forming a strong physical or chemical bond with carbon dioxide. In the desorption process, external energy is applied to the absorbent that is in contact with carbon dioxide, so that the absorbent is regenerated and only pure carbon dioxide is extracted.

To stably reduce a large amount of carbon dioxide and to reduce the amount of carbon dioxide discharged without being captured, it is inevitably necessary to use an absorbent having a strong bonding force with carbon dioxide. However, a process of desorbing captured carbon dioxide consumes a considerable amount of energy, and a process that produces a large amount of energy may involve the generation of carbon dioxide. Accordingly, it is possible to form a circulation structure that generates more carbon dioxide while reducing already-generated carbon dioxide. Therefore, when considering the reduction of carbon dioxide in the entire atmosphere of the earth, it is undesirable to use absorbents having a strong bonding force with carbon dioxide.

On the contrary, when an absorbent having a weak bonding force with carbon dioxide is used, energy consumed in the extraction of carbon dioxide and the regeneration of the absorbent is reduced. However, since it is difficult to capture carbon dioxide at a high rate to a desired level from flue gas supplied at a high flow rate, carbon dioxide may be released without being sufficiently captured.

Furthermore, when such a problem is solved by increasing the residence time of carbon dioxide in a collector, it is necessary to expand the size of the collector. In this case, space and cost problems arise due to additional equipment. In addition, to increase the fluidity of carbon dioxide supplied into the larger collector, flue gas must be supplied to the collector at a higher pressure. At this time, as back pressure applied to the collector increases, a capture process may become unstable, and equipment may be damaged and/or destroyed.

Recently, techniques for converting carbon dioxide in the atmosphere into useful byproducts such as bicarbonate ions and using bicarbonate ions to culture algae have been introduced. However, the concentration of carbon dioxide in the atmosphere is about 400 ppm, so the amount of carbon dioxide is too small to use for converting carbon dioxide in the atmosphere into useful byproducts such as bicarbonate ions. Also, as described above, when carbon dioxide captured from flue gas is regenerated and then converted, conversion efficiency is relatively low as compared with the amount of carbon dioxide supplied. Thereby, a large amount of the supplied carbon dioxide may be released back into the atmosphere.

Therefore, it is necessary to develop a system capable of capturing carbon dioxide contained in flue gas discharged at a high rate with high efficiency, stably capturing carbon dioxide by preventing a sudden increase in back pressure, and at the same time, obtaining a useful byproduct which may be applied to various fields.

DISCLOSURE

Technical Problem

Therefore, the present invention has been made in view of the above problems, and it is an objective of the present invention to provide a carbon dioxide conversion reactor capable of converting carbon dioxide contained in flue gas into an aqueous bicarbonate solution that may be used in many applications; and at the same time, preventing back pressure from increasing due to supplied flue gas by allowing a conversion process to proceed rapidly, thereby significantly reducing the level of carbon dioxide contained in flue gas with high efficiency and high conversion speed, and a process of converting carbon dioxide using the carbon dioxide conversion reactor.

It is another objective of the present invention to provide a series reactor for capturing and converting carbon dioxide using the carbon dioxide conversion reactor of the present invention, the series reactor capable of converting and reducing carbon dioxide, and at the same time, stably capturing and reducing carbon dioxide by preventing the generation of back pressure.

It is still another objective of the present invention to provide a series reactor for converting and capturing carbon dioxide, capable of significantly reducing the concentration of carbon dioxide contained in flue gas discharged into the atmosphere, and at the same time, collecting industrial byproducts generated during a reduction process, which may be used in many applications, and significantly reducing a load in a process of converting and capturing carbon dioxide, and a process of converting and capturing carbon dioxide using the series reactor.

Technical Solution

One aspect of the present invention provides a carbon dioxide conversion reactor, including a gas supply part configured to supply flue gas containing carbon dioxide; an enzyme reaction part including a liquid filling a part of the conversion reactor and a structure provided with carbonic anhydrase for a reaction of converting the supplied carbon dioxide into bicarbonate ions; and a gas discharge part configured to discharge flue gas containing unreacted carbon dioxide from the enzyme reaction part to the outside.

According to a preferred embodiment of the present invention, the carbon dioxide conversion reactor may further include an aqueous bicarbonate solution discharge part configured to discharge an aqueous bicarbonate solution converted and dissolved in the enzyme reaction part.

According to another preferred embodiment of the present invention, the carbonic anhydrase may include any one or more of wild-type carbonic anhydrase and carbonic anhydrase variants. In this case, the wild-type carbonic anhydrase may include any one or more of the group consisting of α-type, β-type, γ-type, δ-type, ε-type, and recombinant carbonic anhydrase.

According to another preferred embodiment of the present invention, a gas supply part and a gas discharge part may be disposed above the interface between liquid and gas inside the conversion reactor, so that back pressure is prevented from increasing due to flue gas supplied to the conversion reactor, and the structure may be positioned at the interface to promote the conversion of carbon dioxide. In addition, the structure may further include a body part including the carbonic anhydrase and at least one float coupled to the body part to position the body part at the interface. In addition, the carbonic anhydrase may be bound to the body part or contained in the body part. In addition, the body part may include a flow path configured to allow the liquid and the carbon dioxide to contact the carbonic anhydrase.

According to another preferred embodiment of the present invention, the carbonic anhydrase may be provided in any one or more of the form of an enzyme aggregate, in which a plurality of carbonic anhydrase enzymes are unbound and aggregated, and the form of a cross-linked enzyme complex, in which a plurality of carbonic anhydrase enzymes are mutually linked.

According to another preferred embodiment of the present invention, the structure may further include a body part and a support, the carbonic anhydrase may be bound to the support or carried in the support, and the support may be bound to the body part or contained in the body part. In this case, the support may include any one or more selected from the group consisting of polymer fiber, electroconductive polymers, porous particles, spherical particles, nanoparticles, beads, carbon nanotubes, wires, pillars, graphene, fullerenes, and polydopamine.

According to another preferred embodiment of the present invention, the cross-linked enzyme complex further includes a first support including first functional groups on a surface thereof; a plurality of first carbonic anhydrase enzymes, wherein each of the plurality of first carbonic anhydrase enzymes is directly bound to each of the first functional groups; and second cross-linked carbonic anhydrase complexes, which are bound to the plurality of first carbonic anhydrase enzymes and formed by cross-linking between adjacent carbonic anhydrase enzymes. In addition, the cross-linked enzyme complex may further include second supports including second functional groups on a surface thereof, which are bound to any one or more of the plurality of first carbonic anhydrase enzymes and the second cross-linked carbonic anhydrase complexes via the second functional groups.

According to another preferred embodiment of the present invention, the carbon dioxide conversion reactor may further include any one or more of an aqueous bicarbonate solution storage part and an aqueous bicarbonate solution utilization part, which are configured to be connected to the aqueous bicarbonate solution discharge part.

Another aspect of the present invention provides a carbon dioxide conversion reactor, including a gas supply part configured to supply flue gas containing carbon dioxide; a carbon dioxide conversion part including a liquid filling a part of the conversion reactor to dissolve and convert the supplied carbon dioxide; and a gas discharge part configured to discharge flue gas containing unreacted carbon dioxide from the carbon dioxide conversion part to the outside.

Still another aspect of the present invention provides a carbon dioxide conversion reactor, including a gas supply part configured to supply flue gas containing carbon dioxide; a carbon dioxide conversion part including a liquid filling a part of the conversion reactor and carbonic anhydrase to dissolve and convert the supplied carbon dioxide; and a gas discharge part configured to discharge flue gas containing unreacted carbon dioxide from the carbon dioxide conversion part to the outside.

Yet another aspect of the present invention provides a process of converting carbon dioxide, including (1) a step of supplying flue gas into the gas supply part of the carbon dioxide conversion reactor according to the present invention; and (2) a step, in which a portion of carbon dioxide contained in the supplied flue gas is converted into bicarbonate ions, and flue gas containing unreacted residual carbon dioxide is discharged through a gas discharge part.

According to a preferred embodiment of the present invention, in step (1), to prevent back pressure from increasing due to the flue gas supplied to the conversion reactor, the flue gas may be supplied from a region above a liquid contained in the conversion reactor, and the conversion of carbon dioxide contained in the supplied flue gas into bicarbonate ions may be promoted by carbonic anhydrase provided in a structure positioned at the interface between the liquid and the gas contained the conversion reactor.

Yet another aspect of the present invention provides a series reactor for converting and capturing carbon dioxide, including the conversion reactor according to the present invention; and a capture reactor configured to capture supplied carbon dioxide, which is connected to the conversion reactor. In the series reactor, flue gas containing carbon dioxide is supplied to the conversion reactor or the capture reactor, in which the carbon dioxide is converted or captured, and then flue gas containing unreacted carbon dioxide is supplied to the capture reactor or the conversion reactor, in which the unreacted carbon dioxide is captured or converted.

According to a preferred embodiment of the present invention, the capture reactor may include carbon dioxide absorbents or carbon dioxide separation membranes.

According to another preferred embodiment of the present invention, the capture reactor may further include a carbon dioxide capture product discharge part configured to discharge capture products containing any one or more of reaction products generated by a binding reaction between the carbon dioxide absorbent and carbon dioxide, and a carbon dioxide desorption device configured to separate and collect carbon dioxide from the discharged capture products, which is connected to the carbon dioxide capture product discharge part.

Yet another aspect of the present invention provides a series reactor for converting and capturing carbon dioxide, including a conversion reactor including an enzyme reaction part provided with a liquid filling a part of the conversion reactor and carbonic anhydrase for a reaction of converting supplied carbon dioxide into bicarbonate ions; and a capture reactor configured to capture the supplied carbon dioxide, which is connected to the conversion reactor.

According to a preferred embodiment of the present invention, flue gas containing carbon dioxide may be supplied to the conversion reactor or the capture reactor, in which the carbon dioxide is converted or captured, and then flue gas containing unreacted carbon dioxide may be supplied to the capture reactor or the conversion reactor, in which the unreacted carbon dioxide is captured or converted.

According to another preferred embodiment of the present invention, the conversion reactor may include a gas supply part configured to supply flue gas, and a gas discharge part configured to discharge flue gas containing unreacted carbon dioxide.

According to another preferred embodiment of the present invention, the carbonic anhydrase may include any one or more of wild-type carbonic anhydrase and carbonic anhydrase variants. In this case, the wild-type carbonic anhydrase may include any one or more of the group consisting of α-type, β-type, γ-type, δ-type, ε-type, and recombinant carbonic anhydrase.

According to another preferred embodiment of the present invention, the carbonic anhydrase may be included as any one or more of the form of free enzymes, in which a plurality of carbonic anhydrase enzymes are dispersed in a liquid phase, the form of an enzyme aggregate, in which a plurality of carbonic anhydrase enzymes are unbound and aggregated, and the form of a cross-linked enzyme complex, in which a plurality of carbonic anhydrase enzymes are mutually linked. In this case, the carbonic anhydrase may be bound to a support or carried in the support.

According to another preferred embodiment of the present invention, the cross-linked enzyme complex further includes a first support including first functional groups on a surface thereof; a plurality of first carbonic anhydrase enzymes, wherein each of the plurality of first carbonic anhydrase enzymes is directly bound to each of the first functional groups; and second cross-linked carbonic anhydrase complexes, which are bound to the plurality of first carbonic anhydrase enzymes and formed by cross-linking between adjacent carbonic anhydrase enzymes. In addition, the cross-linked enzyme complex may further include second supports including second functional groups on a surface thereof, which are bound to any one or more of the plurality of first carbonic anhydrase enzymes and the second cross-linked carbonic anhydrase complexes via the second functional groups.

According to another preferred embodiment of the present invention, the conversion reactor may further include an aqueous bicarbonate solution discharge part configured to discharge an aqueous bicarbonate solution converted and dissolved in the enzyme reaction part.

According to another preferred embodiment of the present invention, the capture reactor may include any one or more of carbon dioxide absorbents and carbon dioxide separation membranes.

According to another preferred embodiment of the present invention, the carbon dioxide conversion reactor may further include any one or more of an aqueous bicarbonate solution storage part and an aqueous bicarbonate solution utilization part, which are configured to be connected to the aqueous bicarbonate solution discharge part.

According to another preferred embodiment of the present invention, the capture reactor may further include a carbon dioxide capture product discharge part configured to discharge capture products containing any one or more of reaction products generated by a binding reaction between the carbon dioxide absorbent and carbon dioxide.

According to another preferred embodiment of the present invention, a carbon dioxide desorption device, which separates and collects carbon dioxide from discharged capture products, and is connected to the carbon dioxide capture product discharge part, may be further included.

Yet another aspect of the present invention provides a series reactor for converting and capturing carbon dioxide, including a conversion reactor including a liquid filling a part of the conversion reactor for a reaction of converting supplied carbon dioxide into bicarbonate ions; and a capture reactor configured to capture the supplied carbon dioxide, which is connected to the conversion reactor.

Yet another aspect of the present invention provides a process of converting and capturing carbon dioxide through a series reactor, the process including (A) a step, in which flue gas containing carbon dioxide is supplied to the conversion reactor of the series reactor according to the present invention, and a portion of the carbon dioxide is converted into bicarbonate ions; and (B) a step, in which flue gas containing unreacted residual carbon dioxide is supplied to a capture reactor to capture the carbon dioxide.

Yet another aspect of the present invention provides a process of converting and capturing carbon dioxide through a series reactor, the process including: (a) a step, in which flue gas containing carbon dioxide is supplied to the capture reactor of the series reactor according to the present invention, and a portion of the carbon dioxide is captured; and (b) a step, in which flue gas containing uncaptured residual carbon dioxide is supplied to a conversion reactor, and the carbon dioxide is converted into bicarbonate ions.

According to a preferred embodiment of the present invention, the process of converting and capturing carbon dioxide through a series reactor may further include a step of discharging the converted bicarbonate ions from the conversion reactor and collecting the discharged bicarbonate ions; and a step of desorbing the captured carbon dioxide and collecting the desorbed carbon dioxide.

In this case, the process of separating captured carbon dioxide may be performed at a temperature ranging from 70 to 130° C.

Hereinafter, terms used in the present invention will be described.

The term "on A" used in the present invention refers to both 'directly on the surface of A' and 'indirectly via B'.

Advantageous Effects

The carbon dioxide conversion reactor according to the present invention can convert carbon dioxide contained in flue gas into a useful byproduct while preventing back pressure from increasing due to supplied flue gas by allowing a conversion process to proceed rapidly, thereby significantly reducing the level of carbon dioxide contained in flue gas with high efficiency and high conversion speed. In addition, the carbon dioxide conversion reactor can be applied to a series reactor capable of converting and reducing carbon dioxide, and at the same time, stably capturing and reducing carbon dioxide by preventing the generation of back pressure. The carbon dioxide conversion reactor is suitable for maximizing the synergistic effect of a process of reducing carbon dioxide through conversion and capture of carbon dioxide. The series reactor according to one embodiment of the present invention rapidly primarily converts a high concentration of carbon dioxide generated in an emission source, and thus a capture process can be performed on unconverted carbon dioxide while preventing an increase in back pressure. Accordingly, when the series reactor is used, unreacted carbon dioxide generated due to thermodynamic limitations in the conversion process can be reduced through the carbon dioxide capture process. In addition, since carbon dioxide is primarily reduced in the conversion process, only unreacted carbon dioxide is supplied to the capture process, resulting in a significant reduction in the load in the capture process. In addition, since carbon dioxide is primarily reduced in the conversion process, carbon dioxide can be efficiently reduced even when an absorbent having a relatively weak bonding force against carbon dioxide is used in the capture process, thereby reducing energy used for regenerating the absorbent and extracting carbon dioxide after capturing carbon dioxide. In addition, byproducts generated during the process of reducing carbon dioxide can be used in various fields. Therefore, it is possible to obtain an economic benefit by creating added values while preventing environmental pollution by reducing carbon dioxide.

BEST MODE

Figure 1:
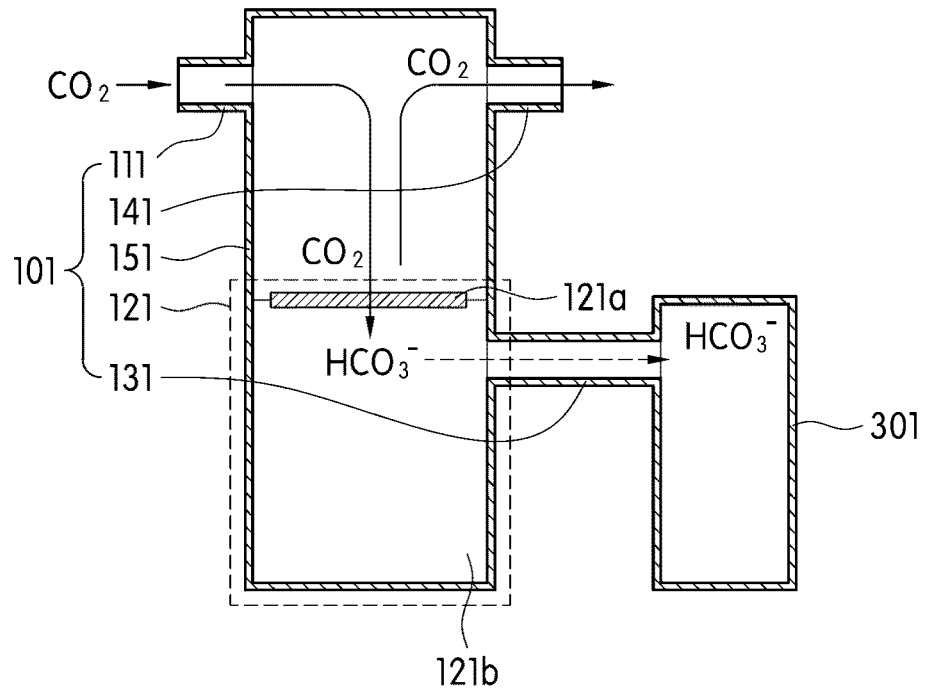
FIG. 1 is a schematic diagram illustrating the carbon dioxide conversion reactor according to a preferred embodiment of the present invention.

Hereinafter, preferred embodiments of the present invention will be described in detail with reference to the accompanying drawings, and those skilled in the art can easily implement the present invention based on the embodiments. The present invention may be embodied in many different forms and is not limited to the embodiments described herein. To clearly describe the present invention, a part unrelated to the description is omitted in the drawings, and the same reference numerals are used for the same or similar components throughout the specification.

As illustrated in FIG. 1, a conversion reactor 101 according to one embodiment of the present invention includes a reaction chamber 151 having an empty internal space in which supplied carbon dioxide resides and an enzyme reaction part 121 is provided; a gas supply part 111 disposed at one side of the reaction chamber 151 to supply flue gas containing carbon dioxide into the reaction chamber 151; the enzyme reaction part 121 for promoting a reaction of converting carbon dioxide contained in supplied flue gas into bicarbonate ions; and a gas discharge part 141 for discharging flue gas containing unreacted carbon dioxide from the enzyme reaction part 121 to the outside, and may further include an aqueous bicarbonate solution discharge part 131 for discharging converted bicarbonate ions to the outside; and an aqueous bicarbonate solution storage part 301 directly connected to the aqueous bicarbonate solution discharge part 131. The conversion reactor 101 serves to convert a high concentration of carbon dioxide contained in flue gas into bicarbonate ions. Such a carbon dioxide conversion process is environmentally friendly compared to other methods of carbon dioxide reduction and/or conversion processes. Further, since carbon dioxide is converted into industrially usable bicarbonate ions, added value may be created, which is very advantageous in terms of economics and productivity. In addition, since carbonic anhydrase can theoretically convert one million carbon dioxide molecules into bicarbonate ions per second, carbonic anhydrase is well suited for the conversion of carbon dioxide that is introduced at a high rate, thereby preventing an increase in back pressure applied to the reactor. Further, there is an advantage that no additional process, such as desorbing carbon dioxide separated and captured from flue gas, is required.

The constituents of the conversion reactor 101 will be described below in accordance with an order from when flue gas is initially supplied to when the flue gas is discharged. The flue gas discharged from carbon dioxide generating sources such as a thermal power plant is supplied to the gas supply unit 111 of the conversion reactor 101. In this case, the gas supply part 111 may be disposed above the interface between a liquid 121b and gas present in the conversion reactor 101. Flue gas containing carbon dioxide supplied through the gas supply part 111 does not have a fluid flow, in which the flue gas passes through the liquid 121b of the enzyme reaction part 121 described below and is discharged to a gas discharge part 141, but may have a fluid flow, in which the flue gas is supplied from above the liquid 121b, passes through above the liquid 121b, and is discharged to the gas discharge part 141 disposed above the liquid. When the gas supply part 111 and the gas discharge part 141 are disposed in consideration of the height of the liquid 121b in the reaction chamber 151 to have such a fluid flow, the supplied flue gas may more easily reside in and pass through the inside of the reactor. Therefore, it is possible to remarkably reduce an increase in the back pressure caused by the resistance of flue gas flow generated while passing through the liquid.

Next, carbon dioxide contained in flue gas supplied to the gas supply part 111 may be converted into bicarbonate ions through a structure 121a including a carbonic anhydrase aggregate and the liquid 121b, which are included in the enzyme reaction part 121, resulting in reduction of carbon dioxide.

The liquid 121b functions as a mediator and/or a reaction material for converting carbon dioxide into bicarbonate ions. Solvents (or solutions) capable of dissolving bicarbonate ions after conversion may be used as the liquid 121b without limitation, and non-limiting examples of the solvents (or solutions) may include water and/or conventional buffer solutions, and non-limiting examples of the buffer solutions may include 2-amino-2-hydroxymethyl-1,3-propanediol.

The structure 121a includes carbonic anhydrase responsible for promoting the conversion of carbon dioxide into bicarbonate ions. The structure 121a including carbonic anhydrase may be disposed in a region of the interior of the liquid 121b or may be uniformly dispersed in the liquid 121b. However, preferably, when the position of the gas supply part is disposed above the liquid 121b and flue gas is supplied from above the liquid to reduce back pressure, to increase a carbon dioxide conversion rate by carbonic anhydrase, the structure 121a is preferably located at the interface between the liquid and gas.

Any known enzymes capable of promoting a reaction of converting carbon dioxide into bicarbonate ions may be used without limitation as the carbonic anhydrase, and for example, the carbonic anhydrase may include any one or more of wild-type carbonic anhydrase and carbonic anhydrase variants. In this case, the wild-type carbonic anhydrase may be enzymes present in natural organisms, such as animals and plants, and may be one or more species selected from the group consisting of α-type, β-type, γ-type, δ-type, and ε-type carbonic anhydrase, and/or may mimic an enzyme present in vivo or may be prepared by artificially recombining the enzyme, or may be a combination of these enzymes and in vivo carbonic anhydrase. The artificial recombinant carbonic anhydrase may be a known one, and thus the amino acid sequence thereof is not particularly limited in the present invention. In addition, in the carbonic anhydrase variants, a portion or all of the amino acid sequence of the native carbonic anhydrase is modified, and the variants may have the basic functions of carbonic anhydrase and may have physical properties such as heat resistance that the native carbonic anhydrase does not possess. In the present invention, the amino acid sequence thereof is not particularly limited.

The carbonic anhydrase may be included as one or more of the form of free enzymes, in which a plurality of carbonic anhydrase enzymes are dispersed in the structure, the form of an enzyme aggregate, in which a plurality of carbonic anhydrase enzymes are unbound and aggregated, and the form of a cross-linked enzyme complex, in which a plurality of carbonic anhydrase enzymes are mutually linked.

In addition, the carbonic anhydrase may be included in the structure with a support, or may be included in the structure without a support.

First, in the case where a support is provided, the carbonic anhydrase may be bound to the support or carried in the support.

The support may serve to bind carbonic anhydrase to the structure or to support carbonic anhydrase on the structure, may be a base upon which carbonic anhydrase may be integrated, and may function to protect carbonic anhydrase from an external force. In addition, when carbonic anhydrase is in the form of an aggregate or a cross-linked complex, the support may serve to stably maintain the forms and to evenly disperse carbonic anhydrase in the structure. Any material that does not inhibit enzymatic activity may be used as the support without limitation, and the shape of the support may be in the form of a bead, fiber, a plate, and the like without any particular limitation. For example, the support may be any one or more selected from the group consisting of polymer fiber, electroconductive polymers, porous particles, spherical particles, nanoparticles, beads, carbon nanotubes, wires, pillars, graphene, fullerenes, and polydopamine. Furthermore, the size of the support may be differently designed according to the specific structure and shape of the conversion reactor, and thus the size of the support is not particularly limited in the present invention.

When carbonic anhydrase is bound to a support, the carbonic anhydrase may be immobilized on the support by physical bonding (e.g., adsorption) and/or by chemical bonding (e.g., ionic bonding, covalent bonding, and the like) via specific functional groups provided on the support. In addition, the carbonic anhydrase may be attached to the support by an adhesive material based on a catechol group such as polydopamine and polynorepinephrine. When the support has a porous structure, carbonic anhydrase may be provided in pores or cavities present in the support, and preferably, is provided in the form of an aggregate or a cross-linked complex. The supported carbonic anhydrase may be bound to the surface of pores or cavities present in the support or may be accommodated in a non-bonded state, but the present invention is not limited thereto.

Meanwhile, the optimal conditions for a reaction of converting carbon dioxide into bicarbonate ions may be different from the optimal conditions for maintaining the enzymatic activity of carbonic anhydrase. In some cases, the environment within a conversion reactor may not be suitable for maintaining the enzymatic activity of carbonic anhydrase. Thus, carbonic anhydrase provided in an enzyme reaction part may be in the form of a cross-linked enzyme complex. Specifically, as shown in FIG. 2, a cross-linked enzyme complex 1000 may be realized with a first support 1010 including first functional groups 1001 is provided on the surface thereof and connected to a plurality of first carbonic anhydrase enzymes 1100 immobilized on the first functional groups 1001, and a plurality of second carbonic anhydrase enzymes 1210,1211,1212, and 1213 which form a cross-linked complex by cross-linking between adjacent carbonic anhydrase enzymes.

The first functional groups 1001 provided on the surface of the support 1010 may be any functional group capable of immobilizing the plurality of first carbonic anhydrase enzymes 1100 without limitation. For example, the first functional groups 1001 may be any one or more selected from the group consisting of a carboxyl group, an amine group, an imine group, an epoxy group, a hydroxyl group, an aldehyde group, a carbonyl group, an ester group, a methoxy group, an ethoxy group, a peroxy group, an ether group, an acetyl group, a sulfide group, a phosphate group, and an iodine group, and is preferably any one or more of a carboxyl group and an amine group.

Figure 2:
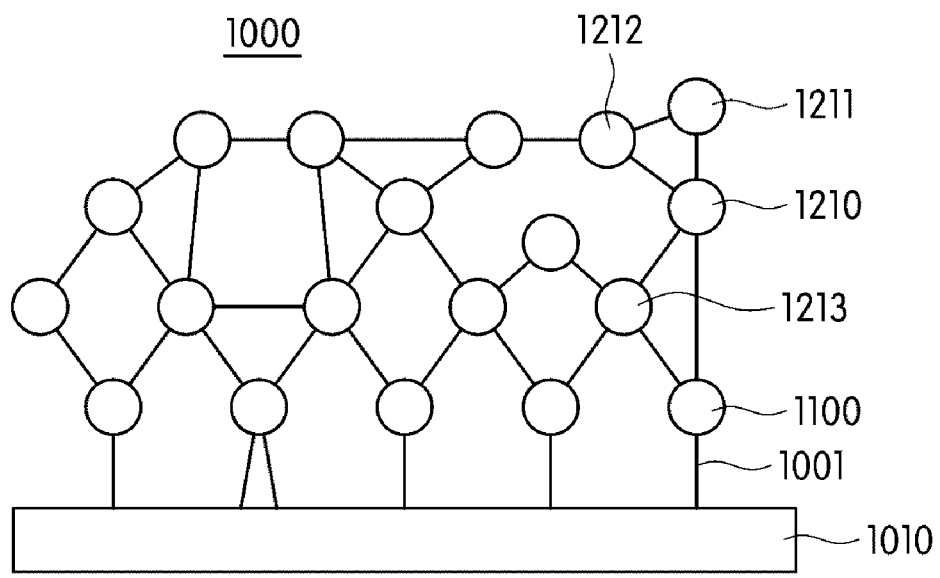
FIGS. 2 and 3 are cross-sectional views illustrating the carbonic anhydrase aggregate according to a preferred embodiment of the present invention.

When carbonic anhydrase forms a cross-linked carbonic anhydrase complex 1000 having a structure as shown in FIG. 2, carbonic anhydrase may stably exhibit and maintain a high enzymatic activity for a long period of time even under temperature and pH conditions which may not be suitable for maintaining/exerting the activity of carbonic anhydrase.

The cross-linked carbonic anhydrase complex 1000 shown in FIG. 2 may be prepared by the same method as in Example 1 described below. In this case, the cross-linked carbonic anhydrase complex shown in FIG. 2 may be prepared by adding only a crosslinking agent without adding a precipitating agent. However, when a precipitating agent is added, a cross-linked carbonic anhydrase complex in which carbonic anhydrase is integrated at a higher density may be prepared. However, the method of preparing the cross-linked carbonic anhydrase complex as shown in FIG. 2 is not limited to Example 1, and the preparation methods disclosed in Korean Patent Publication Nos. 10-2011-0128182, 10-2011-0128134, 10-2013-0127916, and the like, which were invented by the present inventors, may be referred to.

Meanwhile, to stably maintain enzymatic activity for a long period of time while exerting high enzymatic activity, the amount of enzyme bound to the complex should be sufficient, and an appropriate binding force is required so that enzyme does not fall off from the complex due to an external force or the like.

Figure 3:
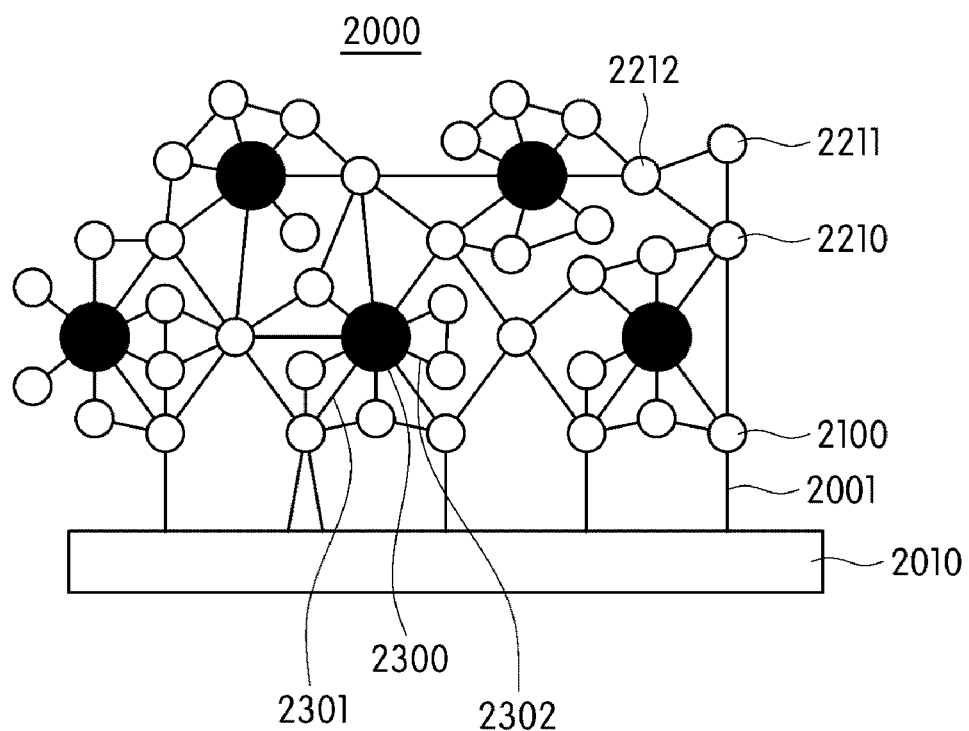

Accordingly, more preferably, as shown in FIG. 3, in addition to a first support 2010, on which first functional groups 2001 are provided, a cross-linked carbonic anhydrase complex 2000 may further include supports 2300, on which second functional groups 2301 and 2302 are provided. A plurality of first carbonic anhydrase enzymes 2100 and second cross-linked carbonic anhydrase complexes 2211, 2212, and 2213 may be connected to the second supports 2300 via the second functional groups.

Since the second cross-linked carbonic anhydrase complex is formed through cross-linking between the enzymes and then through a covalent bond mediated by the second support, the enzymes may bind with strong binding forces. Also, since each of the plurality of second supports 2300 may function as a point capable of forming a covalent bond and may form a cluster with the enzymes, large amounts of enzymes may be incorporated into the complex by clustering. As a result, enzymatic activity may be improved and enzymatic activity may be stably maintained. The description for the second supports 2300 is the same as that for the above-described support (the first support). A material used to prepare the first support may be the same as or different from that used to prepare the second support, and the shape and size of the first support may be the same or different from those of the second support, and a material used to prepare the first support, and the shape and size of the first support are not particularly limited in the present invention. In addition, the description for the second functional groups is the same as that for the functional groups of the above-described support, and the first functional groups may be the same as or different from the second functional groups. Meanwhile, the second supports 2300 of FIG. 3 may be magnetic supports. In this case, when a liquid 121b, in which bicarbonate ions converted in a conversion reactor 101 are dissolved, is discharged through a bicarbonate ion discharge part 131, magnetic forces may be used to prevent the carbonic anhydrase complex from being discharged, or the carbonic anhydrase complex contained in the discharged liquid may be separated and recycled.

The cross-linked carbonic anhydrase complex 2000 according to FIG. 3 may be prepared by the method according to Example 2 described below. As in the case of the carbonic anhydrase complex according to FIG. 2, it is also possible to realize the complex as shown in FIG. 3 by simply adding a crosslinking agent without a precipitating agent. However, when a precipitating agent is added, a complex in which carbonic anhydrase is integrated at a higher density may be prepared, thereby improving physical properties. The method of preparing the cross-linked carbonic anhydrase complex as shown in FIG. 3 is not limited to Example 2, and the preparation methods disclosed in Korean Patent Publication Nos. 10-2011-0128182, 10-2011-0128134, 10-2013-0127916, and the like, which were invented by the present inventors, may be referred to.

Carbonic anhydrase is provided on or carried in the support, and the support including carbonic anhydrase is bounded to or contained in the structure, so that carbonic anhydrase may be provided in the enzyme reaction part. In this case, the bond between the support and the structure may be a physical and/or chemical bond or a bond using an adhesive material, without being limited thereto.

In addition, the carbonic anhydrase may be provided in the structure without a support. When the structure described below includes a body part, the carbonic anhydrase may be included by being bound to or contained in the body part. The carbonic anhydrase may be immobilized on the support by physical bonding (e.g., adsorption) and/or by chemical bonding (e.g., ionic bonding, covalent bonding, and the like) via specific functional groups provided on the body part. In addition, the carbonic anhydrase may be attached to the body part by an adhesive material based on a catechol group such as polydopamine and polynorepinephrine. When the body part has a porous structure, carbonic anhydrase may be provided in pores or cavities present in the body part, and preferably, is provided in the form of an aggregate or a cross-linked complex. The supported carbonic anhydrase may be bound to the surface of pores or cavities present in the body part or may be accommodated in a non-bonded state, but the present invention is not limited thereto.

Meanwhile, considering the supply amount and the supply speed of flue gas, since flue gas is supplied from the upper part of the interface of the liquid 121b in the reaction chamber 151, passes through and is discharged through the reaction chamber, the residence time of the flue gas in the reaction chamber 151 is shortened. Therefore, the residence time required to convert carbon dioxide contained in the flue gas to the desired level may not be secured. That is, when flue gas passes through the liquid 121b and a fluid flow is formed in the conversion reactor 101, back pressure may be generated and increased due to fluid resistance generated in the liquid. Therefore, it is advantageous to dispose the gas supply part 111 at the upper part of the interface of the liquid 121b as described above in terms of preventing an increase in back pressure. In this case, the conversion reaction of supplied carbon dioxide occurs in a limited region, i.e., the liquid interface of the enzyme reaction part, and the residence time of the gas in the reactor is also very short. On the other hand, when the carbonic anhydrase aggregate for promoting the conversion of carbon dioxide is located at a lower portion of the reaction chamber 151 away from the interface of the liquid or is uniformly dispersed throughout the liquid, it may be difficult to convert carbon dioxide in a fast-passing flue-gas to the desired level. In addition, when the residence time of flue gas is increased to solve this problem, back pressure in the conversion reactor may increase. [78]

According to a preferred embodiment of the present invention, the structure 121a provided with carbonic anhydrase may be disposed at the liquid-gas interface as in FIG. 1. Thus, a reaction for converting carbon dioxide may be promoted more actively at the interface. Eventually, increases in conversion and reduction efficiency of carbon dioxide and the occurrence or increase of back pressure may be minimized or prevented.

To dispose the structure 121a at the liquid 121b-gas interface, the structure 121a may be fixed to the side of the reaction chamber 151 at the height of the interface. In this case, there is a difficulty in maintaining the height of the liquid 121b in the reaction chamber 151 at a constant level. Therefore, preferably, the structure 121a may be designed to float on the liquid.

Figure 4:
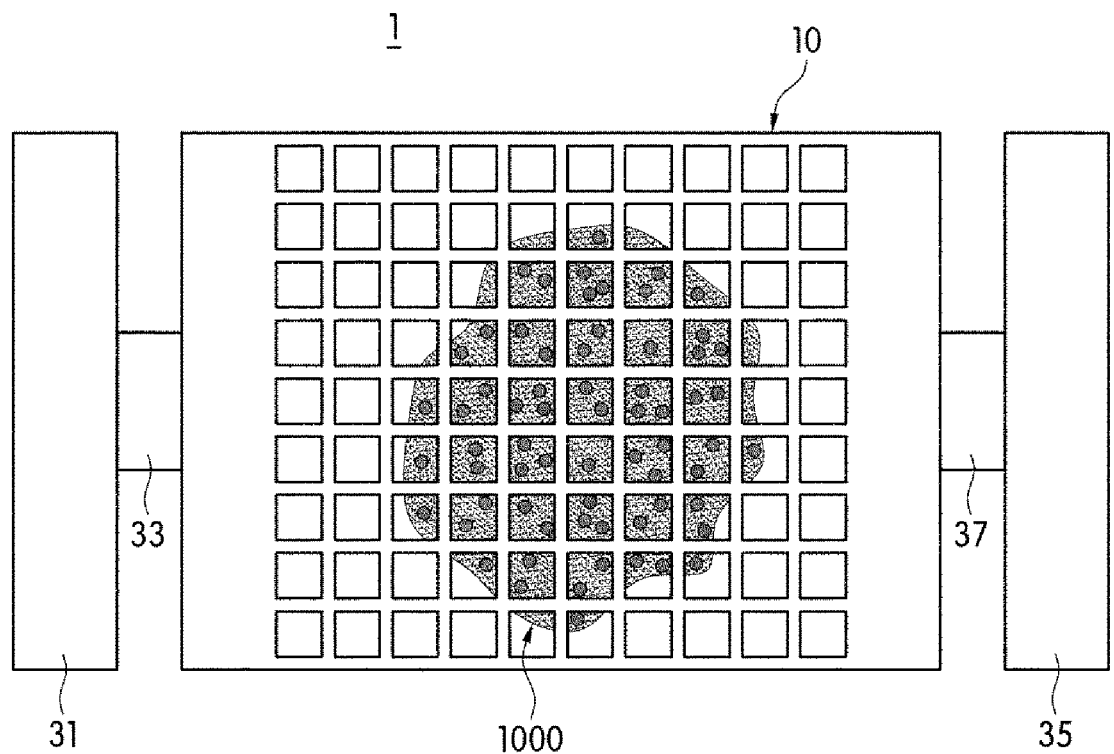
FIG. 4 is a top view illustrating a structure provided with the carbonic anhydrase complex according to a preferred embodiment of the present invention.

For example, as shown in FIG. 4, a structure 1 may include a body part 10 including the cross-linked carbonic anhydrase complex 1000 and one or more floating parts 31 and 35 coupled to the body part 10 to allow the body part 10 to float on the liquid 121b.

Figure 5:
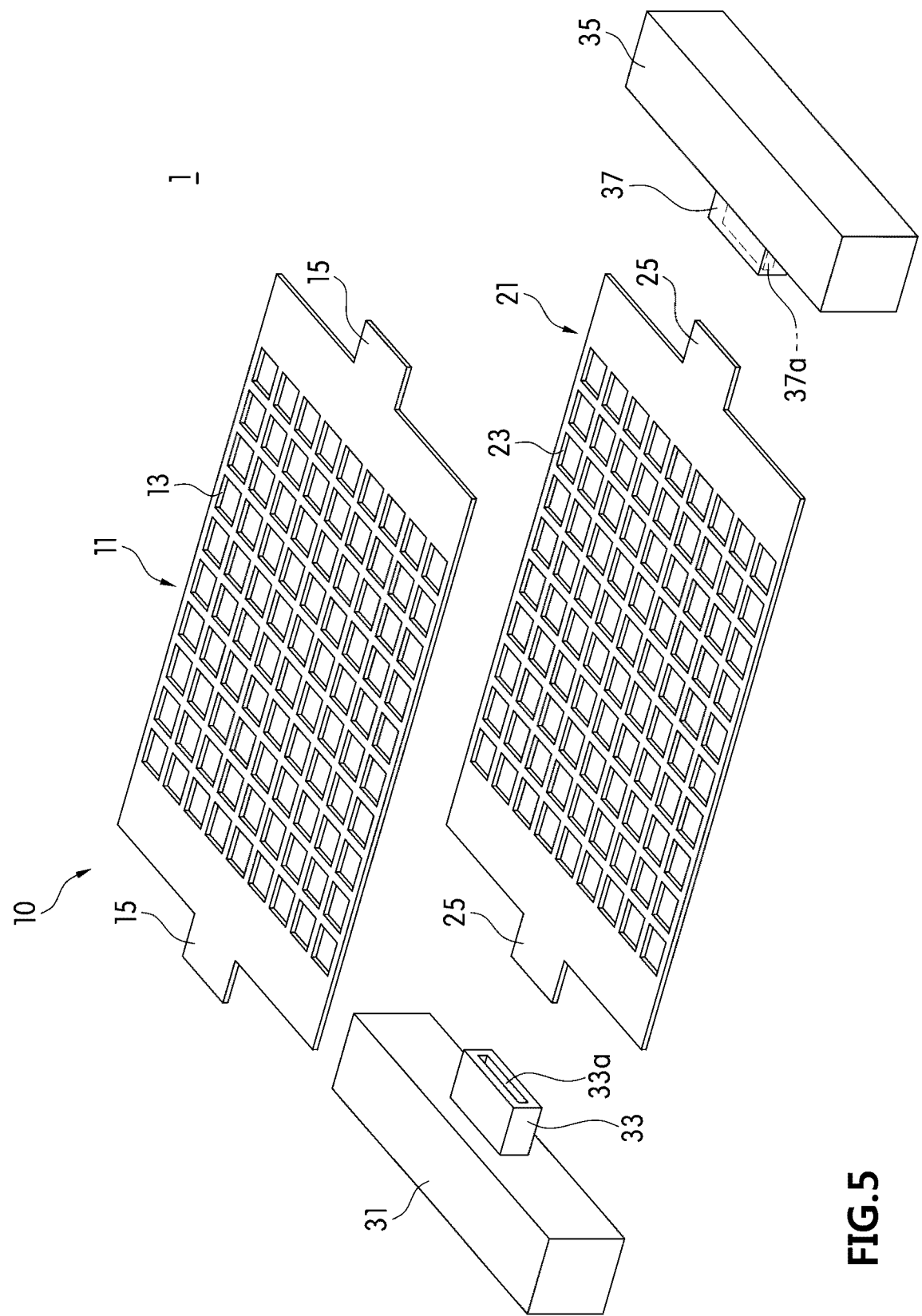
FIG. 5 is an exploded perspective view of the structure according to a preferred embodiment of the present invention.

More specifically, referring to FIG. 5, a first body 11 and a second body 21 may be arranged in parallel to each other in the vertical direction, and each may have a planar structure in the form of a lattice.

In this case, the second body 21 may be disposed adjacent to the surface of the liquid. For example, the second body 21 may be immersed in the liquid or may float on the liquid.

As shown in FIG. 5, the first body 11 and the second body 21 have a single structure separated from each other and are arranged in parallel to each other. However, the first body 11 and the second body 21 may be integrally formed.

In one embodiment of the present invention, protrusion parts 15 and 25 may formed at both ends of the body part 10 to be coupled to the floating parts 31 and 35. In one embodiment of the present invention, the protrusions 15 and 25 of the body 10 are inserted into the coupling grooves 33a and 37a of the floating parts 31 and 35 to be coupled, without being limited thereto.

In this case, the body part 10, that is, the first body 11 and the second body 21, may be formed of at least one of acrylonitrile-butadiene-styrene, polythiophene, polylactic acid, polyvinyl alcohol, polycaprolactam, polycaprolactone, polylactic-co-glycolic acid, polyacrylonitrile, polyester, polyethylene, polyethylene imine, polypropylene oxide, polyurethane, polyglycolic acid, polyethylene terephthalate, polymethyl methacrylate, polystyrene, polydimethylsiloxane, polystyrene-co-maleic anhydride, Teflon, collagen, nylon, cellulose, chitosan, glass, gold, silver, aluminum, iron, copper, and silicon, and may be directly coupled to the cross-linked carbonic anhydrase complex 1000.

In addition, a first float 31 of the floating parts 31 and 35 may be coupled to the end region of the body part 10, e.g., the left end region of the body part 10 as shown in FIG. 5, and a second float 35 may be coupled to the other end region of the body part, e.g., the right end region of the body part as shown in FIG. 5.

Meanwhile, as shown in FIG. 5, in one embodiment of the present invention, the first float 31 and the second float 35 may be formed in a rectangular parallelepiped shape so that the float 31 and the second float 35 can be filled with air. Thus, the structure 1 according to an embodiment of the present invention may float on the liquid.

In one embodiment of the present invention, the first float 31 and the second float 35 may be in any form as long as the floats are made of a material that can be placed on the liquid.

Referring to FIG. 5, in one embodiment of the present invention, protrusion parts 33 and 37 may be formed in a rectangular parallelepiped shape in the first float 31 and the second float 35, respectively.

In this case, the protrusion parts 33 and 37 may be formed on one side (e.g., the left or right side) at which the first float 31 is coupled to the body part 10.

In addition, referring to FIG. 5, the protrusion parts 33 and 37 may be formed with the coupling grooves 33a and 37a, into which the protrusion parts 15 and 25 of the body part 10 are inserted and fitted. In this case, the coupling grooves 33a and 37a may be formed to correspond to the protrusion parts to be fitted to the protrusion parts 15 and 25.

Meanwhile, in one embodiment of the present invention, the first float 31 and the second float 35 may be formed of at least one of acrylonitrile-butadiene-styrene, polythiophene, polylactic acid, polyvinyl alcohol, polycaprolactam, polycaprolactone, polylactic-co-glycolic acid, polyacrylonitrile, polyester, polyethylene, polyethylene imine, polypropylene oxide, polyurethane, polyglycolic acid, polyethylene terephthalate, polymethyl methacrylate, polystyrene, polydimethylsiloxane, polystyrene-co-maleic anhydride, Teflon, collagen, nylon, cellulose, chitosan, glass, gold, silver, aluminum, iron, copper, and silicon.

As shown in FIGS. 4 and 5, the cross-linked carbonic anhydrase complex 1000 may be contained between a first body 11 and a second body 21 constituting the body part 10 or may be bound to the body part 10. In this case, the complex may be bonded to the body part 10 through adhesion using an adhesive material, physical bonding (e.g., adsorption), and/or chemical bonding (e.g., ionic bonding, covalent bonding, etc.) via functional groups provided in the body part 10 or may be physically contained in the body part 10 in an unbounded state. In addition, the portion of the cross-linked carbonic anhydrase complex 1000 bonded to the body part 10 may be carbonic anhydrase and/or a further provided support.

In addition, the body part 10 may include flow paths for allowing carbon dioxide and liquid to flow into the carbonic anhydrase complex 1000. For example, as shown in FIGS. 4 and 5, in the body part, flow paths may be formed in a plurality of mesh-shaped grids.

In addition, as shown in FIG. 1, the conversion reactor 101 may discharge an aqueous bicarbonate solution, in which converted bicarbonate ions are dissolved, through an aqueous bicarbonate solution discharge part 131. The discharged bicarbonate ions may be collected in the separate aqueous bicarbonate solution storage part 301 connected to the aqueous bicarbonate solution discharge part 131, and/or may be used in an aqueous bicarbonate solution utilization part connected to the aqueous bicarbonate solution discharge part 131. In the aqueous bicarbonate solution utilization part, converted and/or collected bicarbonate ions may be synthesized as a carbonate, without being limited thereto. Carbonates may be used as a raw material for microbial cultivation, removal of metal cations, and purification of radioactive materials.

In addition, unlike FIG. 1, the conversion reactor according to another embodiment of the present invention includes a liquid filling a part of the conversion reactor for a reaction of converting supplied carbon dioxide into bicarbonate ions. Specifically, the conversion reactor includes a gas supply part configured to supply flue gas containing carbon dioxide; a carbon dioxide conversion part including a liquid filling a part of the conversion reactor to dissolve and convert the supplied carbon dioxide; and a gas discharge part configured to discharge flue gas containing unreacted carbon dioxide from the carbon dioxide conversion part to the outside.

In addition, the conversion reactor according to another embodiment of the present invention further includes carbonic anhydrase. Specifically, the conversion reactor includes a gas supply part configured to supply flue gas containing carbon dioxide; an enzyme reaction part provided with a liquid filling a part of the conversion reactor and carbonic anhydrase for a reaction of converting supplied carbon dioxide into bicarbonate ions; and a gas discharge part configured to discharge flue gas containing unreacted carbon dioxide from the enzyme reaction part to the outside.

A method of converting carbon dioxide using the conversion reactor according to one preferred embodiment of the present invention is described below. The method may include (1) a step of supplying flue gas into the gas supply part 111 of the conversion reactor 101; and (2) a step, in which a portion of carbon dioxide contained in the supplied flue gas is converted into bicarbonate ions through a liquid filling a part of the conversion reactor or through an enzyme reactor 121, and flue gas containing unreacted residual carbon dioxide is discharged through the gas discharge part 141.

The detailed description of steps (1) and (2) is the same as that of the above-described conversion reactor, and thus is omitted. Step (2) may preferably be performed at a pH ranging from 7.5 to 8.5 and at a temperature ranging from 25 to 45° C. in the conversion reactor.

In addition, in step (1), to prevent back pressure from increasing due to the flue gas supplied to the conversion reactor, the flue gas may be supplied from a region above a liquid contained in the conversion reactor, and the conversion of carbon dioxide contained in the supplied flue gas into bicarbonate ions may be promoted by carbonic anhydrase provided in a structure positioned at the interface between the liquid and the gas contained the conversion reactor.

Meanwhile, the present invention provides a series reactor for converting and capturing carbon dioxide including the above-described conversion reactor. Since the series reactor includes the conversion reactor, the efficiency of reducing carbon dioxide may be increased and an increase in back pressure may be suppressed.

Figure 6:
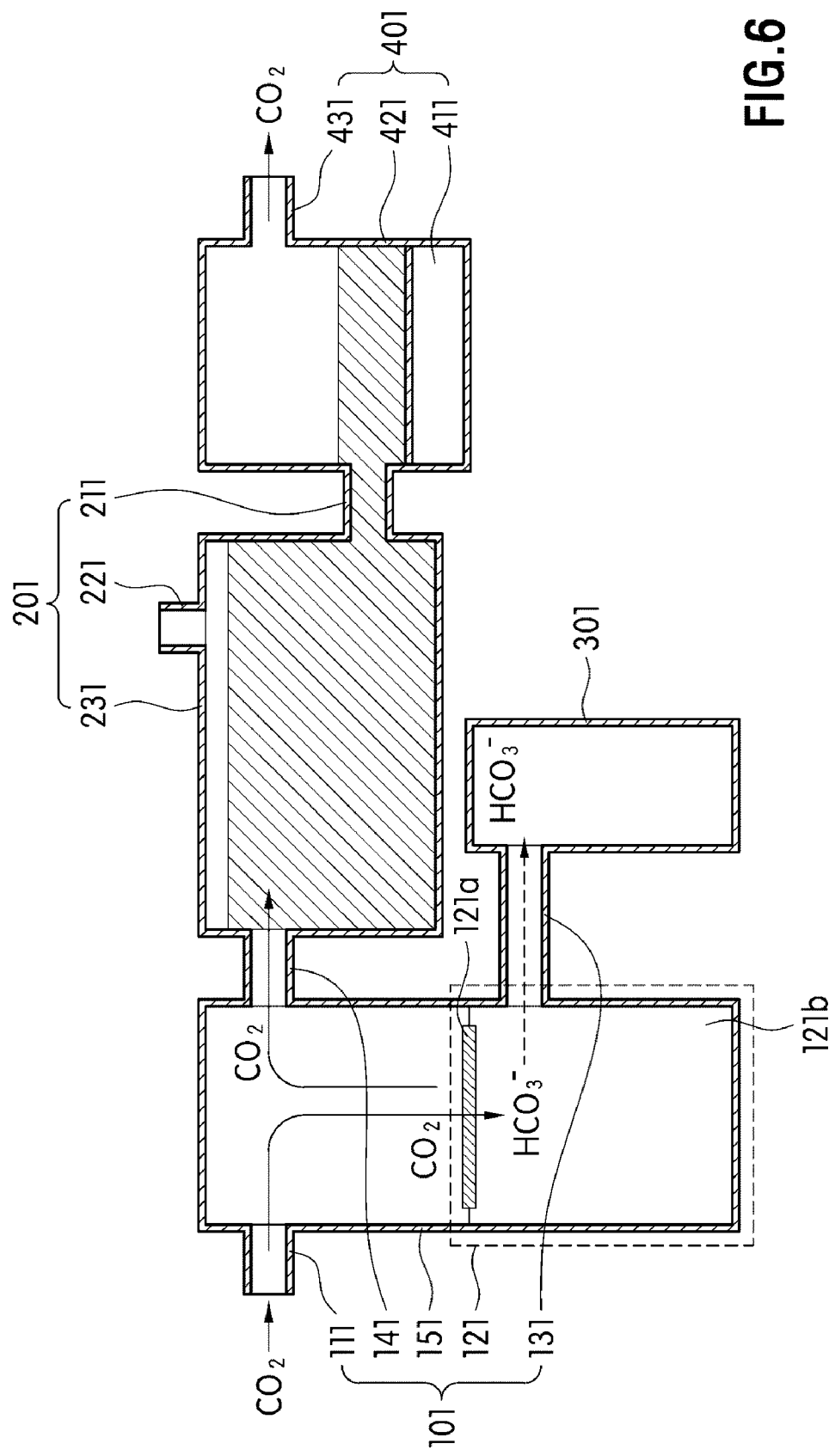
FIGS. 6 and 7 are schematic diagrams showing the series reactor according to a preferred embodiment of the present invention, in which a process of converting and capturing carbon dioxide proceeds differently depending on the direction of supply of flue gas containing carbon dioxide.
Figure 7:
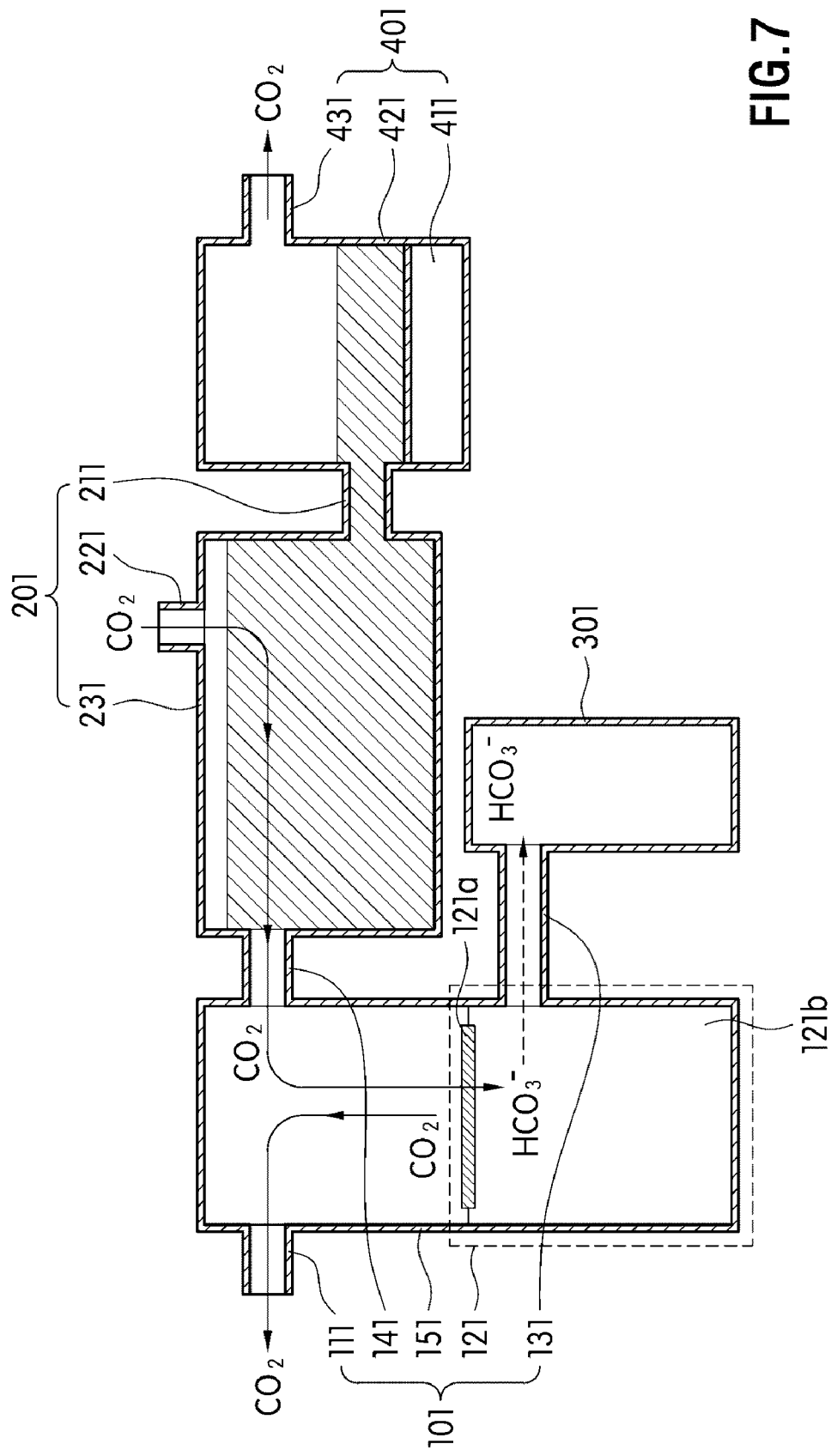

As shown in FIGS. 6 and 7, the series reactor for converting and capturing carbon dioxide according to one embodiment of the present invention includes the conversion reactor 101 and a capture reactor 201, which are connected with each other so that carbon dioxide may flow from one side to the other side. And the series reactor may further include the aqueous bicarbonate solution storage part 301 for collecting bicarbonate ions converted in the conversion reactor 101 and a carbon dioxide desorption device 401 for separating and collecting carbon dioxide captured in the capture reactor 201.

A carbon dioxide flow in the series reactor and the resulting reaction are described below. As shown in FIG. 6, in the series reactor in which a fluid flow of carbon dioxide is generated, flue gas containing carbon dioxide is supplied to the conversion reactor 101 through the gas supply part 111, and then the conversion of the carbon dioxide is mediated by the liquid or the enzyme reaction part 121. Then, flue gas containing unreacted carbon dioxide is supplied to the capture reactor 201 through the gas discharge part 141 of the conversion reactor 101 so that unreacted carbon dioxide is captured. Flue gas containing carbon dioxide uncaptured in the capturing process may be discharged through a gas discharge part 221 of the capture reactor 201.

In addition, as shown in FIG. 7, in the series reactor in which a fluid flow of carbon dioxide is generated, flue gas containing carbon dioxide is supplied through a gas supply part 221 of the capture reactor 201, and carbon dioxide is captured. Then, uncaptured carbon dioxide is supplied into the conversion reactor 101 through a gas supply part 141, and carbon dioxide is converted via the enzyme reaction part 121. Flue gas containing unreacted carbon dioxide may be discharged through a gas discharge part 111 of the conversion reactor 101.

In contrast to conventional carbon dioxide reducing devices or converting devices, considering the fast flow rate of supplied flue gas and back pressure generated in the reactor, the carbon dioxide conversion/capture capacity of the reactor itself, and flue-gas retention time in the reactor required to convert and capture carbon dioxide to the desired level, the series reactor having a flow of supplied flue gas, such as in FIGS. 6 and 7, may significantly reduce back pressure generated in the reactor, and may have high efficiency in reducing and converting carbon dioxide.

Specifically, conventional carbon dioxide reducing devices use an absorber or a separation membrane to reduce carbon dioxide. In this case, due to the low efficiency, the absorber or separation membrane needs a certain amount of time to capture carbon dioxide from flue gas. Furthermore, at the current level of technology development, the separation membrane has low efficiency in separating carbon dioxide and other gases such as nitrogen. Accordingly, to capture the entire amount of carbon dioxide contained in flue gas, it is required not only to use an absorbent or separation membrane having a high capture efficiency but also to keep the flue gas in the reactor for a predetermined time or longer. However, considering the amount of flue gas discharged from thermal power plants, etc. and the rapid flow rate, when a reactor having a limited volume and a limited capture efficiency is used, it is difficult to secure a required residence time in the reactor to capture the entire amount of carbon dioxide contained in flue gas. In addition, since flue gas supplied to the reactor is discharged without being allowed to reside in the reactor for a sufficient time, the discharged flue gas may contain a large amount of uncaptured carbon dioxide. That is, the efficiency of reducing carbon dioxide may be reduced.

When an absorbent having a high capture efficiency is used to solve these problems, a great deal of energy is consumed in the separation process of captured carbon dioxide, and thus carbon dioxide may be generated/discharged during the production of such energy. In addition, when the residence time of carbon dioxide in the reactor is sufficiently secured with another method, the capture efficiency of carbon dioxide may be increased. However, considering the amount and flow rate of flue gas being very quickly discharged, back pressure generated in the reactor may be increased, resulting in destabilization of the capture process and damage/breakage of the reactor.

According to the present invention, the conversion reactor 101 and the capture reactor 201 are connected in series, and supplied flue gas is supplied to the capture reactor 201 or the conversion reactor 101 through the conversion reactor 101 or the capture reactor 201. As a result, the efficiency of reducing carbon dioxide may be greatly improved. In addition, it is possible to obtain a reflex effect that may prolong the residence time of flue gas residing in the entire series reactor. Thus, it is possible to convert/reduce carbon dioxide to the desired level even when discharged flue gas is rapidly supplied in a large amount, and at the same time, back pressure in the reactor may be prevented from increasing. Furthermore, it is possible to prevent a process load that may occur due to the presence of only one of the conversion reactor and the capture reactor.

Furthermore, when the process load is reduced, it may be free from the restriction that the conversion capacity of carbonic anhydrase used in the carbon dioxide conversion and/or capture process and/or the capture capacity of an absorbent must meet a certain level or more. Thus, it is very advantageous in terms of cost reduction in installing and operating the reactor.

In addition, the conversion process of the carbon dioxide using the conversion reactor 101 may reduce carbon dioxide in flue gas and may also produce byproducts which may be utilized for various fields. Thus, it is possible to obtain an economic benefit by creating added values while preventing environmental pollution by reducing carbon dioxide.

In addition, as shown in FIG. 6, when a capture process is performed on unreacted carbon dioxide after reduction of carbon dioxide through the conversion reactor 101, since carbon dioxide in flue gas is primarily reduced in the conversion reactor 101, flue gas discharged from the series reactor contains a very low amount of carbon dioxide, even when an adsorbent having relatively low binding affinity with carbon dioxide is used in the capture reactor 201. Thus, the efficiency of reducing carbon dioxide may be improved. In addition, since less energy is required to separate carbon dioxide bound to the weaker absorbent, it is possible to reduce the amount of carbon dioxide emitted in an energy production process for separating carbon dioxide. Meanwhile, in the case of the series reactor shown in FIG. 6, compared with the series reactor shown in FIG. 7, even when capture efficiency in the capture reactor is relatively small, carbon dioxide may be converted and reduced to a desired level, and at the same time, less energy is consumed in separating carbon dioxide. Therefore, it may be advantageous in economic and environmental aspects.

Cases where any one of the capture reactor and the conversion reactor is provided in a plurality and connected in series are described below. First, when several capture reactors are connected in series, the generation of backpressure may be prevented, but energy required to separate captured carbon dioxide may be increased, which may further increase the generation and release of carbon dioxide. In addition, useful byproducts may not be obtained during a reduction process of capturing carbon dioxide as described below, which may be disadvantageous to the economic benefit of creating added value. On the other hand, when several conversion reactors are connected in series, considering the reduction efficiency of carbon dioxide through the conversion reactors, the number of conversion reactors to be provided may be remarkably increased. Such an increase in equipment may result in an increase in the size of the apparatus and an increase in equipment cost. In addition, when the conversion reaction of carbon dioxide is a reversible reaction, there is a limit to the efficiency of reducing carbon dioxide.

On the other hand, to attain reduction of equipment and conversion/capture of carbon dioxide at the same time, a method of causing a carbon dioxide capture reaction and a carbon dioxide conversion reaction to occur in one reactor may be considered. For example, one reactor may be provided with both carbon dioxide absorbent and carbonic anhydrase. However, since most of absorbent solutions are at a high temperature of 40 to 60° C. and the pH range of the absorbent solutions is about 9 to 12, these conditions are not a suitable environment for the long-term activity of carbonic anhydrase. Therefore, enzymatic activity is rapidly lost and thus the enzymatic activity may not be stably maintained for a long period of time, and frequent enzyme replacement is required, which may lead to an increase in conversion cost. In addition, even when carbonic anhydrase is provided under the above conditions, since carbon dioxide contained in flue gas is very concentrated, the amount of carbon dioxide discharged with flue gas increases without being captured due to a high load in a carbon dioxide capture process. Thus, it may be difficult to reduce the amount of carbon dioxide in flue gas.

Each configuration of the series reactor will be described below based on the flow of flue gas shown in FIG. 6. First, flue gas containing carbon dioxide is supplied to the conversion reactor 101, and carbon dioxide is converted into bicarbonate ions, thereby obtaining useful byproducts and at the same time reducing carbon dioxide. The description of the conversion reactor 101 is the same as that described above and thus is omitted. Flue gas containing carbon dioxide unreacted in the liquid or the enzyme reaction part 121 of the conversion reactor 101 may be supplied to the capture reactor 201 through a gas discharge part 141.

Next, the capture reactor 201 connected in series with the above-described conversion reactor 101 is described below.

The capture reactor 201 serves to capture carbon dioxide unreacted in the conversion reactor 101. When flue gas containing carbon dioxide is supplied to the inside of a reaction chamber 231 of the capture reactor 201 through the gas discharge part 141 of the conversion reactor 101, the supplied carbon dioxide is captured in the reactor, and then flue gas containing uncaptured carbon dioxide may be discharged to the outside through the gas discharge part 221 of the capture reactor 201. The capture reactor 201 may separate and capture carbon dioxide through a carbon dioxide separation membrane and/or a carbon dioxide absorbent.

The carbon dioxide separation membrane may be a conventional carbon dioxide separation membrane, and a carbon dioxide separation membrane known in the art may be used without limitation. Non-limiting examples of materials used for the carbon dioxide separation membrane may include 6FDA-based polyimide with excellent separation properties of $CO_2/N2$ as an organic polymer, and cardo-type polyimide, polysulfone, and cellulose acetate, and the like. In addition, specific examples for the structure of the carbon dioxide separation membrane may include a structure including a porous inorganic film applied on porous steel or a ceramic support, or a polymer membrane structure having selective permeability by glassy polymers or rubbery polymers, without being limited thereto. In addition, considering a mechanism by which the separation membrane acts, when the separation membrane is the porous inorganic membrane, the mechanism may be classified into Knudsen diffusion depending on molecular weight, surface diffusion due to surface attraction, capillary condensation, and a molecular sieve mechanism depending on molecular size, without being limited thereto. Depending on the purpose, a suitable separation membrane may be selected and used.

The carbon dioxide absorbent may be a conventional carbon dioxide absorbent, and may specifically include any one or more of dry absorbents and wet absorbents. Examples of the dry absorbent may include solid amines, alkali metal salts, alkaline earth metal salts, zeolites, metal organic structures, and the like. In addition, the wet absorbent may be a conventional wetting agent, preferably an amine-based aqueous solution, and may include any one selected from the group consisting of monoethanolamine, diethanolamine, dimethylethanolamine, diethylethanolamine, dimethylglycine, N-methyldiethanolamine, 2-amino-methyl-1-propanol, 2-amino-hydroxymethyl-1,3-propanediol, piperidine, piperazine, potassium carbonate, sodium carbonate, ammonia, and ammonium carbonate.

According to a preferred embodiment of the present invention, when the capture reactor includes a carbon dioxide absorbent, preferably a wet absorbent, a cross-linked carbonic anhydrase complex may be further included. When the cross-linked carbonic anhydrase complex is provided in the capture reactor, the efficiency of capturing carbon dioxide may be improved, and the rate of capturing carbon dioxide may be increased. However, the carbon dioxide capture environment in the capture reactor may be an alkaline condition with a pH of 9 to 12 and a temperature of 40 to 60° C. Under such conditions, denaturation of carbonic anhydrase may occur and the enzymatic activity may be significantly reduced. Therefore, to stably maintain excellent enzymatic activity for a long period of time, carbonic anhydrase contained in the capture reactor may be different from carbonic anhydrase contained in the conversion reactor, and preferably, the cross-linked carbonic anhydrase complex formed by cross-linking carbonic anhydrase enzymes as shown in FIGS. 3 and 4 may be advantageous. Carbon dioxide is supplied from the conversion reactor 101 to the capture reactor 201, and capture products including any one or more of reaction products generated by a binding reaction between the carbon dioxide absorbent and carbon dioxide is discharged through a capture product discharge part, and the capture products is supplied to the carbon dioxide desorption device 401 for separating and collecting carbon dioxide. Flue gas containing residual carbon dioxide excluding captured carbon dioxide of flue gas containing carbon dioxide supplied from the conversion reactor 101 may be finally discharged into the atmosphere through a flue gas discharge part 221 or may be supplied again to the gas supply part 111 of the conversion reactor 101 to repeat the carbon dioxide reduction process.

The carbon dioxide desorption device 401 may include a chamber 421 for storing supplied capture products and separated carbon dioxide, and an energy supply part 411 for generating energy, e.g., heat, required for a process of separating carbon dioxide, and may be provided with a carbon dioxide discharge part 431 for discharging the separated carbon dioxide. In this case, applied heat may be 40 to 60° C., without being limited thereto, and may be changed depending on the type of carbon dioxide absorbent used.

In the series reactor according to the present invention, to produce different types of flue gas flow as shown in FIGS. 6 and 7 using the same series reactor, known methods and configurations may be selected and implemented. For example, in the case of the conversion reactor 101, the gas supply part 111 in FIG. 6 functions as a gas discharge part 111 in FIG. 7, and in the case of the capture reactor 201, the gas discharge part 221 in FIG. 6 functions as the gas supply part 221 in FIG. 7. Alternatively, unlike FIGS. 6 and 7, the conversion reactor and the capture reactor may each include a gas supply part through which flue gas may directly flow, and each gas supply part may be implemented as an openable/closable type. Also, a process of converting and capturing carbon dioxide may be performed in such a manner that, when one side is opened, the other is closed. That is, in consideration of the supply amount of flue gas, the concentration of carbon dioxide, and the required amount of bicarbonate ion, a reactor in which flue gas flows first may be selected. In this case, flue gas may be directly introduced into the selected reactor and the gas supply part(s) provided in remaining unselected reactors may be closed to prevent direct entry of flue gas. Also, opening or closing of the gas supply parts may be controlled in consideration of the amount of flue gas residing in the reactor even during a process of converting and capturing flue gas after flue gas is supplied to the series reactor.

Figure 8:
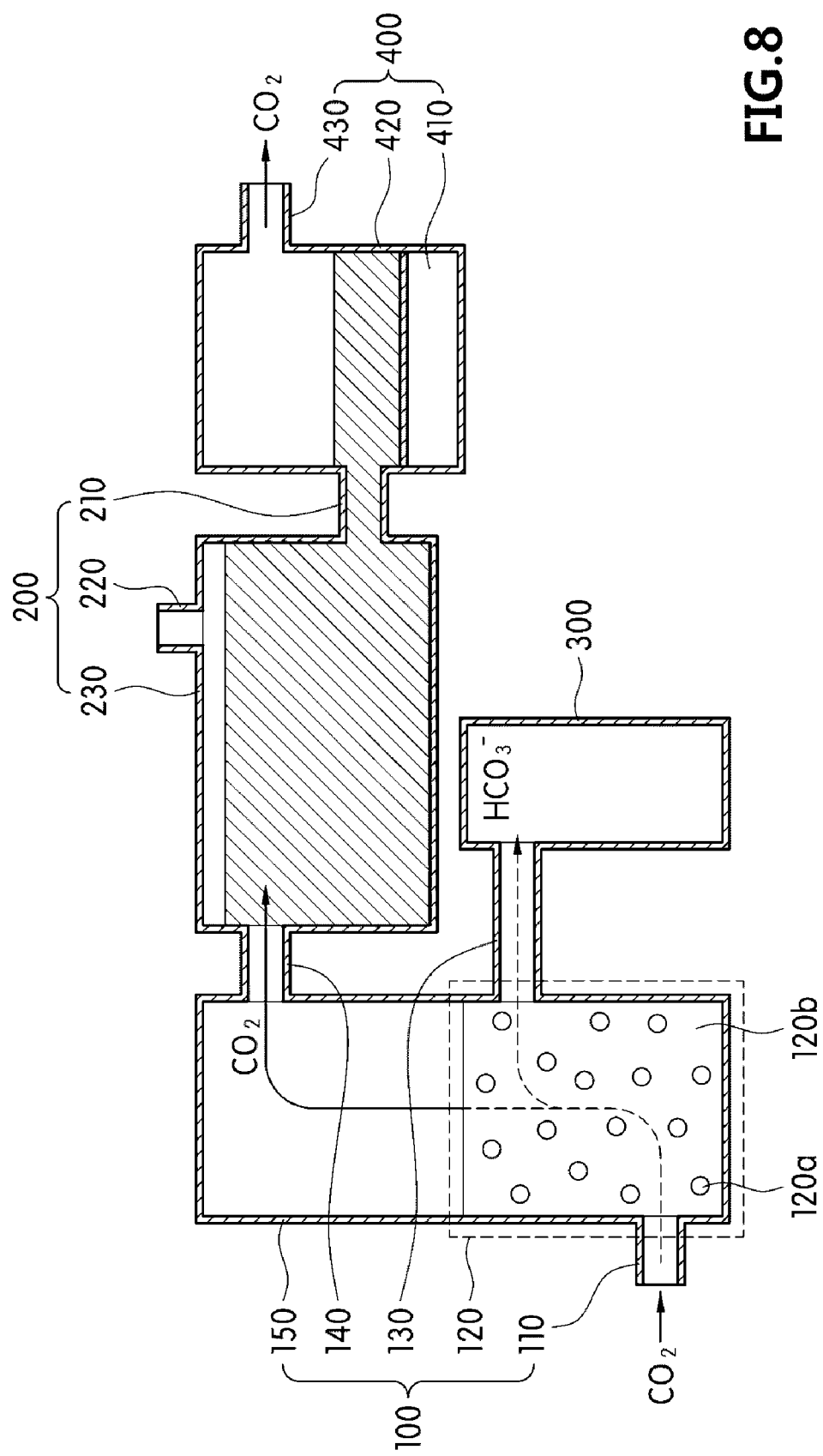
FIGS. 8 and 9 are schematic diagrams showing the series reactor according to a preferred embodiment of the present invention, in which a process of converting and capturing carbon dioxide proceeds differently depending on the direction of supply of flue gas containing carbon dioxide.
Figure 9:
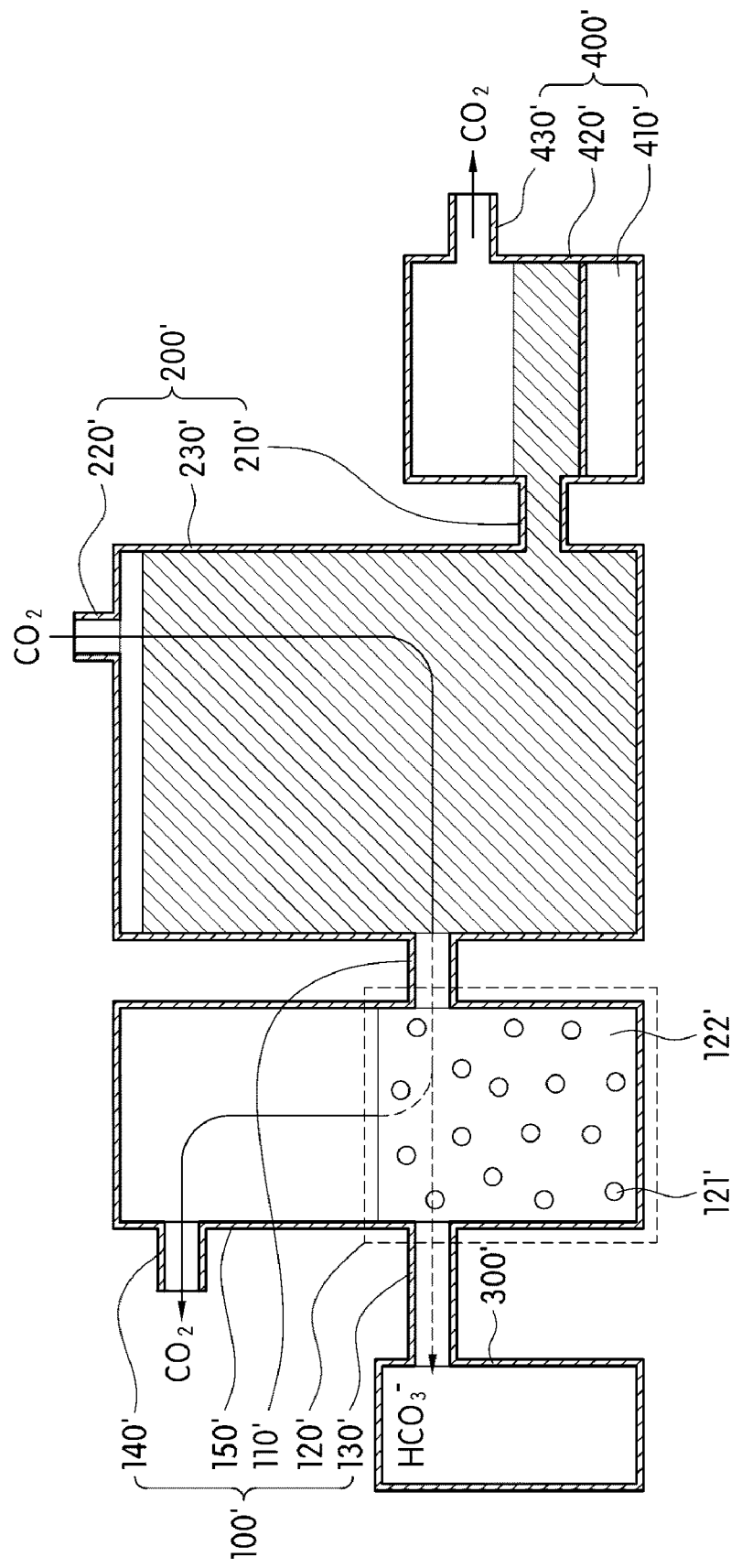

As shown in FIGS. 8 and 9, the series reactor according to another embodiment of the present invention includes conversion reactors 100 and 100' and capture reactors 200 and 200', which are connected with each other so that carbon dioxide may flow from one side to the other side, and may further include bicarbonate ion storage portions 300 and 300' for collecting bicarbonate ions converted in the conversion reactors 100 and 100' and carbon dioxide desorption devices 400 and 400' for separating and collecting carbon dioxide captured in the capture reactors 200 and 200'.

Carbon dioxide flow in the series reactor and a reaction that occurs in accordance with the flow are described below. In the series reactor as shown in FIG. 8, flue gas containing carbon dioxide is supplied to the conversion reactor 100 through a gas supply part 110, carbon dioxide is converted through an enzyme reaction part 120, flue gas containing unreacted carbon dioxide is supplied to a capture reactor 200 through a gas discharge part 140 of the conversion reactor 100 to capture the unreacted carbon dioxide, and flue gas containing uncaptured carbon dioxide is discharged through a gas discharge part 220 of the capture reactor 200.

In addition, in the series reactor as shown in FIG. 9, flue gas containing carbon dioxide is supplied through a gas supply part 220' of a capture reactor 200', carbon dioxide is captured, uncaptured carbon dioxide is supplied to a conversion reactor 100' through a gas supply part 110', carbon dioxide is converted through an enzyme reaction part 120', and flue gas containing unreacted carbon dioxide is discharged through a gas discharge part 140' of a conversion reactor 100'.

In comparison with the series reactor shown in FIG. 9, the series reactor shown in FIG. 8 may convert and reduce carbon dioxide to the target level even when the capture efficiency in the capture reactor is relatively low, and at the same time, less energy may be consumed in separation of captured carbon dioxide. Therefore, the series reactor of FIG. 8 may be advantageous in economic and environmental aspects.

When the series reactors according to another embodiment of the present invention as shown in FIGS. 8 and 9 are compared with the series reactor shown in FIG. 6, the carbon dioxide conversion reactor is different, and the remainder of the configuration is the same. Hereinafter, description of the series reactor according to FIGS. 8 and 9 is described below mainly on differences from the series reactor according to FIG. 6. At this time, the description will be made with reference to FIG. 8.

First, the conversion reactor 100, in which flue gas containing carbon dioxide is initially supplied, is described. The conversion reactor 100 serves to convert a high concentration of carbon dioxide contained in flue gas into bicarbonate ions. Such conversion of carbon dioxide primarily reduces the amount of supplied carbon dioxide. Such a carbon dioxide conversion process is environmentally friendly compared to other methods of carbon dioxide reduction and/or conversion processes. Further, since carbon dioxide is converted into industrially usable bicarbonate ions, added value may be created, which is very advantageous in terms of economics and productivity. In addition, since carbonic anhydrase can theoretically convert one million carbon dioxide molecules into bicarbonate ions per second, carbonic anhydrase is well suited for the conversion of carbon dioxide which is introduced at a high rate, thereby preventing an increase in back pressure applied to the reactor. Further, there is an advantage that an additional process such as desorbing carbon dioxide is not required.

In the series reactor according to the present invention, for a reaction of converting supplied carbon dioxide into bicarbonate ions, the enzyme reaction part 120 including a liquid filling a part of the conversion reactor and carbonic anhydrase for catalyzing the conversion reaction is provided, and the series reactor may include a reaction chamber 150 with an empty interior to accommodate the enzyme reaction part 120, a gas supply part 110 for supplying flue gas containing carbon dioxide, the gas discharge part 140 for discharging flue gas containing unreacted carbon dioxide of carbon dioxide contained in flue gas supplied in the conversion reactor 100 through the gas supply part 110, and the aqueous bicarbonate solution discharge part 130 for discharging an aqueous solution in which bicarbonate ions converted in the enzyme reaction part 120 are dissolved.

Generated flue gas is supplied into the conversion reactor 100 through the gas supply part 110, and the supplied flue gas passes through the enzyme reaction part 120.

The enzyme reaction part 120 serves to primarily reduce carbon dioxide contained in flue gas by converting carbon dioxide contained in flue gas into bicarbonate ions. The enzyme reaction part 120 is a catalyst capable of promoting a reaction of converting carbon dioxide into bicarbonate ions, and includes carbonic anhydrase enzymes 120a and the liquid 120b which mediates the reaction and/or functions as a reactant of the reaction. The carbonic anhydrase enzymes 120a may be included as any one or more of the form of free enzymes, in which a plurality of carbonic anhydrase enzymes are dispersed in a liquid phase, the form of an enzyme aggregate, in which a plurality of carbonic anhydrase enzymes are unbound and aggregated, and the form of a cross-linked enzyme complex, in which a plurality of carbonic anhydrase enzymes are mutually linked. In addition, the carbonic anhydrase enzymes 120a may be provided in the enzyme reaction part 120 provided with a support so that the carbonic anhydrase enzymes 120a may be bound to or carried in the support. Description of the liquid 120b and the carbonic anhydrase enzymes 120a is the same as those described above, and thus is omitted.

The carbonic anhydrase enzymes 120a may be provided in the enzyme reaction part 120 and may promote the conversion of supplied carbon dioxide into bicarbonate ions. The converted bicarbonate ions may be discharged through the aqueous bicarbonate solution discharge part 130, and an aqueous solution containing the discharged bicarbonate ions may be collected in a separate aqueous bicarbonate solution storage part 300 connected to the aqueous bicarbonate solution discharge part 130 of the conversion reactor and/or may be used in a bicarbonate ion utilization part connected to the aqueous bicarbonate solution discharge part 130. In the bicarbonate ion utilization part, converted and/or collected bicarbonate ions may be synthesized as a carbonate, and the carbonate may be used as raw material for microbial cultivation, removal of metal cations, and purification of radioactive materials, without being limited thereto.

In addition, differently from FIG. 1, the above-described conversion reactor may be formed to include a liquid filling a part of the conversion reactor for a reaction of converting supplied carbon dioxide into bicarbonate ions.

Meanwhile, the concentration of convertible carbon dioxide in a liquid filling a part of the conversion reactor 100 or in the enzyme reaction part 120 including the liquid may be limited. Accordingly, when the concentration of carbon dioxide contained in supplied flue gas is high, unreacted carbon dioxide may be present in the enzyme reaction part 120. The unreacted carbon dioxide may be supplied to the capture reactor 200 through a gas discharge part 140 which may be provided in the conversion reactor 100.

Description of the capture reactor 200 is the same as that of the capture reactor 201 in FIG. 6, and thus is omitted.

Unlike FIGS. 8 and 9, in which flue gas is introduced into one of the conversion reactor and the capture reactor, and then the flue gas moves to the other in a sequential manner, in the series reactor according to another preferred embodiment of the present invention, each of the conversion reactor and the capture reactor may include a gas supply part, through which flue gas is directly introduced, and each gas supply part may be implemented as an openable/closable type. Also, a process of converting and capturing carbon dioxide may be performed in such a manner that, when one side is opened, the other is closed. That is, in consideration of the supply amount of flue gas, the concentration of carbon dioxide, and the required amount of bicarbonate ion, a reactor in which flue gas flows first may be selected. In this case, flue gas may be directly introduced into the selected reactor and the gas supply part(s) provided in remaining unselected reactors may be closed to prevent direct entry of flue gas. Also, opening or closing of the gas supply parts may be controlled in consideration of the amount of flue gas residing in the reactor even during a process of converting and capturing flue gas after flue gas is supplied to the series reactor.

When carbon dioxide contained in flue gas is directly supplied to the conversion reactor through the series reactor according to the present invention as shown in FIGS. 6 and 8, a process of converting and capturing carbon dioxide may include (A) a step, in which flue gas containing carbon dioxide is supplied to the conversion reactor of the series reactor according to one embodiment of the present invention, and a portion of the carbon dioxide is converted into bicarbonate ions; and (B) a step, in which flue gas containing unreacted residual carbon dioxide is supplied to a capture reactor to capture the carbon dioxide.

In addition, as shown in FIGS. 7 and 9, when flue gas is directly supplied to the capture reactor, a process of converting and capturing carbon dioxide may include (a) a step, in which flue gas containing carbon dioxide is supplied to the capture reactor of the series reactor according to one embodiment of the present invention, and a portion of the carbon dioxide is captured; and (b) a step, in which flue gas containing uncaptured residual carbon dioxide is supplied to a conversion reactor, and the carbon dioxide is converted into bicarbonate ions.

The process of converting and capturing carbon dioxide is described on the basis of the series reactor in FIG. 6. Detailed description of step (A) is the same as description in the above-described conversion reactor, and is omitted. The process of converting carbon dioxide in the conversion reactor is preferably performed at a pH of 7.5 to 8.5 and at a temperature of 25 to 45° C.

In addition, in step (A), to prevent back pressure from increasing due to the flue gas supplied to the conversion reactor, the flue gas may be supplied from a region above a liquid contained in the conversion reactor, and the conversion of carbon dioxide contained in the supplied flue gas into bicarbonate ions may be promoted by carbonic anhydrase provided in a structure positioned at the interface between the liquid and the gas contained the conversion reactor.

In addition, detailed description of step (B) is the same as description in the above-described capture reactor, and is omitted. The process of capturing carbon dioxide in the capture reactor is preferably performed at a pH of 9 to 12 and at a temperature of 40 to 60° C., more preferably 45 to 55° C. When the process is performed at a temperature of less than 40° C., it is not possible to reduce carbon dioxide to the desired level. On the other hand, when the process is performed at a temperature of exceeding 60° C., the solubility of carbon dioxide is lowered and the amount of carbon dioxide discharged in a gaseous state is remarkably increased. Accordingly, there may be a problem that the amount of unreacted carbon dioxide in the capture reactor significantly increases.

According to a preferred embodiment of the present invention, the process may further include a step, in which carbon dioxide is captured by a carbon dioxide absorbent in the capture reactor, the captured carbon dioxide is discharged, and the carbon dioxide absorbent and the carbon dioxide are separated to collect the carbon dioxide. The process of separating and collecting carbon dioxide may be performed in the carbon dioxide desorption device 401, which may be further provided in the series reactor, without being limited thereto. The carbon dioxide desorption device may be a carbon dioxide desorption device applied to a conventional apparatus for reducing carbon dioxide. Thus, in the present invention, the device is not particularly limited. The amount of energy, such as heat, input for separating carbon dioxide differs depending on the specific type of absorbent provided in the capture reactor, and the separation time may vary depending on the specific type of absorbent, and thus the present invention is not particularly limited thereto.

Modes of the Invention

The present invention will now be described more specifically with reference to the following examples. However, the following examples should not be construed as limiting the scope of the present invention, and should be construed as facilitating understanding of the present invention.

<Preparation Example 1> Preparation of Cross-Linked Carbonic Anhydrase Complex 1

A polymer nanofiber was used as a support provided in a cross-linked carbonic anhydrase complex. Polystyrene (PS, MW=950,400) and poly(styrene-co-maleic anhydride) (PSMA, MW=224,000) were used as a polymer to prepare the polymer nanofiber, and tetrahydrofuran (THF) and acetone were used as an organic solvent to dissolve the polymers. These materials were purchased from Sigma-Aldrich (St. Louis, Mo., USA). An electrospinning method was used to prepare the polymer nanofiber. The voltage operating conditions for electrospinning were 7 kV, and a flow rate of 0.1 ml/hr was applied using a syringe pump.

To prepare the cross-linked carbonic anhydrase complex, the prepared polymer nanofiber was mixed with a solution containing carbonic anhydrase (10 mg/ml, 50 mM sodium phosphate buffer, pH 7.6). A container containing the solution containing carbonic anhydrase and the nanofiber was agitated at 200 rpm for 30 minutes. Then, to induce covalent bonding between carbonic anhydrase and the first functional group, maleic anhydride, present in the polymer nanofiber, the mixture was stirred at 4° C. for 2 hours.

Next, to form the cross-linked carbonic anhydrase complex, 0.5% v/v glutaraldehyde was added as a crosslinking agent, and ammonium sulfate as a precipitating agent was added so as to have a concentration of 45% w/v in solution. Then, the mixture was reacted in a refrigerator at 4° C. for 14 hours to facilitate the formation of the cross-linked complex. Thereafter, a solution containing the cross-linked carbonic anhydrase complex was stirred at 200 rpm for 30 minutes using 100 mM Tris buffer (pH 7.6), followed by washing with 100 mM PB. After processing was completed, the enzyme-immobilized material was stored at 4° C. to prepare the cross-linked carbonic anhydrase complex as shown in FIG. 3

Example 1

To prepare a structure provided with the cross-linked carbonic anhydrase complex prepared in Preparation Example 1, a body part and floating parts having structures as shown in FIG. 5 were prepared. Specifically, an acrylonitrile-butadiene-styrene (ABS) polymer was used as the material of the body part, and the size of the body was 63 mm×21 mm×1 mm, and a lattice used as a flow path was formed into a square shape of 6 mm×6 mm. At this time, the first and second bodies having the same structure were vertically stacked, and the cross-linked carbonic anhydrase complex of Preparation Example 1 was placed between the laminated structures. In addition, an acrylonitrile-butadiene-styrene (ABS) polymer was used as the material of the floating parts, and the floating part was prepared in the form of a rectangular parallelepiped having a size of 21 mm×10 mm×3 mm. At this time, an empty space through which air may enter into the floating parts is formed so that the body part may be positioned at the interface between the liquid and gas when the body part is joined.

To prepare the structure, the cross-linked carbonic anhydrase complex of Preparation Example 1 was placed and fixed between the two stacked body parts in the form of a housing, and both ends of the body part were coupled with the floating parts. Thereafter, a container provided with a gas supply part having a diameter of 9 cm and a height of 22 cm and a diameter of 0.3 cm located at a height of 10 cm and a gas discharge part having the same diameter as that of the gas supply part was prepared, and a Tris-HCl (pH 8.0) solution was added to the container until a height of 5 cm was reached, and then the structure was placed at the interface of the solution. Thereby, a carbon dioxide conversion reactor was prepared.

Example 2

The carbon dioxide conversion reactor was prepared by the same method as in Example 1, except that a structure not containing the cross-linked carbonic anhydrase complex was placed at the interface between the solution and gas.

Experimental Example

A carbon dioxide conversion reaction was induced by supplying gaseous carbon dioxide at a rate of 200 mL/min for 20 minutes through the gas supply part of the carbon dioxide conversion reactor according to the examples. Then, 20 mL of the reaction solution was extracted, and a carbonate was precipitated by reacting with 10 mL of a 670 mM calcium chloride solution. Centrifugation was carried out at 15,000 rpm for 15 minutes and a liquid phase was removed to separate the precipitated carbonate. The separated carbonate was dried in an oven at 90° C. for 24 hours and weighed, and the results are shown in Table 1 below.

TABLE 1

|  | Example 1 | Example 2 |
| --- | --- | --- |
| Weight of converted calcium carbonate (mg) | 214 | 114 |

As can be seen from Table 1, it can be confirmed that the conversion reactor (Example 1) having the cross-linked carbonic anhydrase complex has a conversion efficiency as high as 1.9 times greater than that of the conversion reactor (Example 2) without the cross-linked carbonic anhydrase complex.

Although embodiments of the present invention have been described, the spirit of the present invention is not limited by the embodiments presented in this specification. Those skilled in the art of the present invention can readily suggest another embodiment by adding, modifying, deleting, or adding the components within the scope of the present invention, and this is also included within the spirit of the present invention.

The invention claimed is:

1. A carbon dioxide conversion reactor, comprising:
a gas supply part configured to supply gas containing carbon dioxide;
an enzyme reaction part for a reaction of converting the supplied carbon dioxide into bicarbonate ions comprising a liquid that is filled in a part of the conversion reactor, and a structure; and
a gas discharge part configured to discharge gas containing unreacted carbon dioxide from the enzyme reaction part to the outside,
wherein the structure comprises a body part on which carbonic anhydrase is disposed as an enzyme, and at least one float to position the body part at an interface between the liquid and the gas inside the conversion reactor,
wherein said carbonic anhydrase is immobilized on fiber support,
said body part comprises multiple planar structures, each comprising a lattice portion, with the planar structures arranged in parallel with one another, and vertically stacked, with the fiber support between the planar structures with the lattice portions, and
lattice openings in the lattice portions of the planar structures arranged to provide flow paths for the liquid and gas containing carbon dioxide to contact immobilized carbonic anhydrase on the fiber support.

2. The carbon dioxide conversion reactor according to claim 1, further comprising an aqueous bicarbonate solution discharge part configured to discharge an aqueous bicarbonate solution converted and dissolved in the enzyme reaction part.

3. The carbon dioxide conversion reactor according to claim 1, wherein the carbonic anhydrase comprises any one or more of wild-type carbonic anhydrase and carbonic anhydrase variants.

4. The carbon dioxide conversion reactor according to claim 1, wherein the gas supply part and the gas discharge part are disposed above the interface between the liquid and the gas inside the conversion reactor, so that back pressure is prevented from increasing due to flue gas supplied to the conversion reactor.

5. The carbon dioxide conversion reactor according to claim 1, wherein the carbonic anhydrase is provided in any one or more of a form of an enzyme aggregate, in which a plurality of carbonic anhydrase enzymes are unbound and aggregated, and a form of a cross-linked enzyme complex, in which a plurality of carbonic anhydrase enzymes are mutually linked.

6. The carbon dioxide conversion reactor according to claim 5, wherein the cross-linked enzyme complex further comprises a first support comprising first functional groups on a surface thereof, and a plurality of first carbonic anhydrase enzymes, wherein each of the plurality of first carbonic anhydrase enzymes is directly bound to each of the first functional groups; and
second cross-linked carbonic anhydrase complexes, which are bound to the plurality of first carbonic anhydrase enzymes and formed by cross-linking between adjacent carbonic anhydrase enzymes.

7. The carbon dioxide conversion reactor according to claim 6, wherein the cross-linked enzyme complex further comprises second supports comprising second functional groups on a surface thereof, which are bound to any one or more of the plurality of first carbonic anhydrase enzymes and the second cross-linked carbonic anhydrase complexes via the second functional groups.

8. The carbon dioxide conversion reactor according to claim 2, further comprising any one or more of an aqueous bicarbonate solution storage part and an aqueous bicarbonate solution utilization part, which are configured to be connected to the aqueous bicarbonate solution discharge part.

9. The carbon dioxide conversion reactor according to claim 1, wherein said fiber support comprises electrospun polymer fibers.

10. A series reactor for converting and capturing carbon dioxide, comprising:
the conversion reactor configured to convert supplied carbon dioxide into bicarbonate ions according to claim 1; and
a capture reactor configured to capture supplied carbon dioxide, which is connected to the conversion reactor.

11. The series reactor according to claim 10, wherein the capture reactor contains a carbon dioxide adsorbent and further comprises a carbon dioxide capture product discharge part configured to discharge capture products containing any one or more of reaction products generated by a binding reaction between the carbon dioxide absorbent and carbon dioxide; and a carbon dioxide desorption device configured to separate and collect carbon dioxide from the discharged capture products, which is connected to the carbon dioxide capture product discharge part.

12. The series reactor according to claim 10, wherein gas containing carbon dioxide is supplied to the conversion reactor or the capture reactor, in which the carbon dioxide is converted or captured, and then gas containing unreacted carbon dioxide is supplied to the capture reactor or the conversion reactor, in which the unreacted carbon dioxide is captured or converted.

13. A process of converting carbon dioxide, comprising:
(1) a step of supplying gas into the gas supply part of the carbon dioxide conversion reactor according to claims 1; and
(2) a step, in which a portion of carbon dioxide contained in the supplied gas is converted into bicarbonate ions, and gas containing unreacted residual carbon dioxide is discharged through a gas discharge part.

14. The process of converting carbon dioxide according to claim 13, wherein in step (1), to prevent back pressure from increasing due to the gas supplied to the conversion reactor, the gas is supplied from a region above a liquid contained in the conversion reactor, and conversion of carbon dioxide contained in the supplied gas into bicarbonate ions is promoted by carbonic anhydrase provided in the structure positioned at an interface between the liquid and the gas contained the conversion reactor.

* * * * *

UNITED STATES PATENT AND TRADEMARK OFFICE
CERTIFICATE OF CORRECTION

PATENT NO. : 10,981,111 B2  
APPLICATION NO. : 15/738620  
DATED : April 20, 2021  
INVENTOR(S) : Kim et al.

It is certified that error appears in the above-identified patent and that said Letters Patent is hereby corrected as shown below:

In the Claims

Column 26, Line 44, "claims" should be -- claim --.

Signed and Sealed this  
Thirteenth Day of July, 2021

Drew Hirshfeld  
*Performing the Functions and Duties of the*  
*Under Secretary of Commerce for Intellectual Property and*  
*Director of the United States Patent and Trademark Office*